(12) United States Patent  
Suri

(10) Patent No.: US 8,708,914 B2  
(45) Date of Patent: Apr. 29, 2014

(54) VALIDATION EMBEDDED SEGMENTATION METHOD FOR VASCULAR ULTRASOUND IMAGES

(75) Inventor: Jasjit S. Suri, Roseville, CA (US)

(73) Assignee: Atheropoint, LLC, Roseville, CA (US)

( * ) Notice: Subject to any disclaimer, the term of this patent is extended or adjusted under 35 U.S.C. 154(b) by 635 days.

(21) Appl. No.: 12/960,491

(22) Filed: Dec. 4, 2010

(65) Prior Publication Data
US 2011/0299754 A1 Dec. 8, 2011

Related U.S. Application Data

(63) Continuation-in-part of application No. 12/802,431, filed on Jun. 7, 2010, now Pat. No. 8,313,437, and a continuation-in-part of application No. 12/896,875, filed on Oct. 2, 2010, now Pat. No. 8,485,975.

(51) Int. Cl.
| | |
|---|---|
| A61B 8/00 | (2006.01) |
| G06K 9/00 | (2006.01) |
| A61B 8/08 | (2006.01) |
| G06T 7/00 | (2006.01) |
| A61B 5/02 | (2006.01) |
| A61B 8/14 | (2006.01) |

(52) U.S. Cl.
CPC ............ *A61B 8/085* (2013.01); *A61B 8/5223* (2013.01); *A61B 8/0891* (2013.01); *G06T 7/0012* (2013.01); *G06T 7/0085* (2013.01); G06T 2207/10132 (2013.01); G06T 2207/30101 (2013.01); G06T 2207/20016 (2013.01); *A61B 5/02007* (2013.01); *A61B 8/14* (2013.01); *A61B 8/145* (2013.01)
USPC ............ 600/443; 600/437; 600/465; 382/128

(58) Field of Classification Search
USPC ........................... 600/437, 443, 465; 382/128
See application file for complete search history.

(56) References Cited

U.S. PATENT DOCUMENTS

| | | | |
|---|---|---|---|
| 5,343,867 A | 9/1994 | Shankar | |
| 5,734,739 A | 3/1998 | Sheehan et al. | |

(Continued)

FOREIGN PATENT DOCUMENTS

WO   WO03042921 A   5/2003

OTHER PUBLICATIONS

Gutierrez, Marco et al. "Assessment of carotid diameter and wall thickness in ultrasound images using active contours improved by a multiresolution technique". Medical Imaging 2002: Physiology and Function from Multidimensional Images, Proceedings of SPIE vol. 4683 (2002).*

*Primary Examiner* — Long V. Le  
*Assistant Examiner* — Helene Bor

(57) ABSTRACT

A computer-implemented system and method for intima-media thickness (IMT) measurements using a validation embedded segmentation method. Various embodiments include receiving biomedical imaging data and patient demographic data corresponding to a current scan of a patient; checking the biomedical imaging data in real-time to determine if an artery of the patient has a calcium deposit in a proximal wall of the artery; acquiring arterial data of the patient as a combination of longitudinal B-mode and transverse B-mode data; using a data processor to automatically recognize the artery by embedding anatomic information; using the data processor to calibrate a region of interest around the automatically recognized artery; automatically computing the weak or missing edges of intima-media and media-adventitia walls using edge flow, labeling and connectivity; and determining the intima-media thickness (IMT) of an arterial wall of the automatically recognized artery.

15 Claims, 30 Drawing Sheets

(56) References Cited

U.S. PATENT DOCUMENTS

| | | | |
|---|---|---|---|
| 6,132,373 A | 10/2000 | Ito et al. | |
| 6,251,072 B1 | 6/2001 | Ladak et al. | |
| 6,267,728 B1 | 7/2001 | Hayden | |
| 6,347,152 B1 | 2/2002 | Shinagawa et al. | |
| 6,597,937 B2 | 7/2003 | Liu et al. | |
| 6,614,453 B1 | 9/2003 | Suri et al. | |
| 6,718,055 B1 | 4/2004 | Suri | |
| 6,785,409 B1 | 8/2004 | Suri | |
| 6,813,373 B1 | 11/2004 | Suri et al. | |
| 6,817,982 B2 | 11/2004 | Fritz et al. | |
| 6,835,177 B2 | 12/2004 | Fritz et al. | |
| 6,842,638 B1 | 1/2005 | Suri et al. | |
| 6,845,260 B2 | 1/2005 | Liu et al. | |
| 6,987,568 B2 | 1/2006 | Dana | |
| 7,020,314 B1 | 3/2006 | Suri et al. | |
| 7,024,027 B1 | 4/2006 | Suri et al. | |
| 7,074,187 B2 | 7/2006 | Selzer et al. | |
| 7,090,640 B2 * | 8/2006 | Barth et al. | 600/443 |
| 7,110,000 B2 | 9/2006 | Zhang et al. | |
| 7,149,368 B2 | 12/2006 | Tong et al. | |
| 7,161,601 B2 | 1/2007 | Zhang et al. | |
| 7,272,241 B2 | 9/2007 | Demi et al. | |
| 7,340,083 B2 | 3/2008 | Yuan et al. | |
| 7,353,117 B2 | 4/2008 | Yuan et al. | |
| 7,376,253 B2 | 5/2008 | Spreeuwers et al. | |
| 7,639,261 B2 | 12/2009 | Sekine et al. | |
| 7,657,299 B2 | 2/2010 | Huizenga et al. | |
| 7,680,330 B2 | 3/2010 | Leung | |
| 7,686,764 B2 * | 3/2010 | Watanabe et al. | 600/443 |
| 2003/0053669 A1 | 3/2003 | Suri et al. | |
| 2003/0236460 A1 | 12/2003 | Ma et al. | |
| 2004/0116808 A1 * | 6/2004 | Fritz et al. | 600/437 |
| 2004/0243365 A1 | 12/2004 | Yuan et al. | |
| 2005/0042222 A1 | 2/2005 | Yamamoto et al. | |
| 2005/0043614 A1 | 2/2005 | Huizenga et al. | |
| 2005/0119555 A1 | 6/2005 | Fritz et al. | |
| 2005/0267365 A1 * | 12/2005 | Sokulin et al. | 600/437 |
| 2006/0064016 A1 | 3/2006 | Demi et al. | |
| 2006/0241465 A1 | 10/2006 | Huennekens et al. | |
| 2007/0003116 A1 | 1/2007 | Yuan et al. | |
| 2007/0038061 A1 | 2/2007 | Huennekens et al. | |
| 2007/0269086 A1 | 11/2007 | Kerwin et al. | |
| 2007/0287897 A1 | 12/2007 | Faris | |
| 2008/0009702 A1 | 1/2008 | Liu et al. | |
| 2008/0051658 A1 | 2/2008 | Demi et al. | |
| 2008/0080755 A1 | 4/2008 | Payonk et al. | |
| 2008/0095422 A1 | 4/2008 | Suri et al. | |
| 2008/0145841 A1 | 6/2008 | Libutti et al. | |
| 2008/0171939 A1 | 7/2008 | Ishihara | |
| 2008/0221446 A1 | 9/2008 | Washburn et al. | |
| 2008/0269595 A1 | 10/2008 | Wong | |
| 2008/0274457 A1 | 11/2008 | Eng et al. | |
| 2008/0316374 A1 | 12/2008 | Koike et al. | |
| 2009/0028793 A1 | 1/2009 | Neri et al. | |
| 2009/0252395 A1 | 10/2009 | Chan et al. | |
| 2010/0060644 A1 | 3/2010 | Elie et al. | |
| 2010/0081931 A1 | 4/2010 | Destrempes et al. | |

* cited by examiner

```
Automated Intima-Media Thickness (IMT) Measurement
                Processing Logic
                    -2600-
                       |
                       v
Receive biomedical imaging data and patient demographic
    data corresponding to a current scan of a patient.
                    -2610-
                       |
                       v
     Check the biomedical imaging data in real-time to
 determine if an artery of the patient has a calcium deposit
            in a proximal wall of the artery.
                    -2612-
                       |
                       v
    Acquire arterial data of the patient as a combination of
         longitudinal B-mode and transverse B-mode data.
                    -2614-
                       |
                       v
  Use a data processor to automatically recognize the artery
            by embedding anatomic information.
                    -2616-
                       |
                       v
  Use the data processor to calibrate a region of interest
         around the automatically recognized artery.
                    -2618-
                       |
                       v
  Determine the intima-media thickness (IMT) of an arterial
      wall of the automatically recognized artery.
                    -2620-
                       |
                       v
                     ( End )
```

Figure 26

VALIDATION EMBEDDED SEGMENTATION METHOD FOR VASCULAR ULTRASOUND IMAGES

PRIORITY APPLICATION

This is a continuation-in-part patent application of patent application Ser. No. 12/802,431; filed Jun. 7, 2010 now U.S. Pat. No. 8,313,437 by the same applicant. This is also a continuation-in-part patent application of patent application Ser. No. 12/896,875; filed Oct. 2, 2010 now U.S. Pat. No. 8,485,975 by the same applicant. This present patent application draws priority from the referenced patent applications. The entire disclosures of the referenced patent applications are considered part of the disclosure of the present application and are hereby incorporated by reference herein in its entirety.

COPYRIGHT

A portion of the disclosure of this patent document contains material that is subject to copyright protection. The copyright owner has no objection to the facsimile reproduction of the patent document or the patent disclosure, as it appears in the Patent and Trademark Office patent files or records, but otherwise reserves all copyright rights whatsoever. The following notice applies to the software and data as described below and in the drawings that form a part of this document: Copyright 2009-2010 Jasjit S. Suri, Biomedical Technologies Inc., All Rights Reserved.

TECHNICAL FIELD

This patent application relates to methods and systems for use with data processing, data storage, and imaging systems, according to one embodiment, and more specifically, for ultrasound image processing.

BACKGROUND

Introduction

The state of Atherosclerosis in carotids or other blood vessels can be studied using MRI or Ultrasound. Because ultrasound offers several advantages like real time scanning of carotids, compact in size, low cost, easy to transport (portability), easy availability and visualization of the arteries are possible, Atherosclerosis quantification is taking a new dimension using ultrasound. Because one can achieve compound and harmonic imaging which generates high quality images with ultrasound, it is thus possible to do two-dimensional (2D) and three-dimensional (3D) imaging of carotid ultrasound for monitoring of Atherosclerosis.

In recent years, the possibility of adopting a composite thickness of the tunica intima and media, i.e., an intima-media thickness (hereinafter referred to as an "IMT") of carotid arteries, as surrogate marker for cardiovascular risk and stroke. Conventional methods of imaging a carotid artery using an ultrasound system, and measuring the IMT using an ultrasonic image for the purpose of diagnosis are being developed.

A conventional measuring apparatus can measure an intima-media thickness of a blood vessel using an ultrasound device to scan the blood vessel. Then, for example, an image of a section of the blood vessel including sections of the intima, media and adventitia is obtained. The ultrasound device further produces digital image data representing this image, and outputs the digital image data to a data analyzing device.

The intima, media and adventitia can be discriminated on the basis of changes in density of tissue thereof. A change in density of tissue of the blood vessel appears as a change of luminance values in the digital image data. The data analyzing device detects and calculates the intima-media thickness on the basis of the changes of luminance values in the digital image data. The digital image data can include a plurality of luminance values each corresponding to respective one of a plurality of pixels of the image. The data analyzing device can set a base position between a center of the blood vessel and a position in a vicinity of an inner intimal wall of the blood vessel on the image, on the basis of a moving average of the luminance values. The data analyzing device can detect a maximum value and a minimum value from among the luminance values respectively corresponding to a predetermined number of the pixels arranged from the base position toward a position of an outer adventitial wall on the image. The data analyzing device can then calculate the intima-media thickness on the basis of the maximum value and the minimum value.

The major challenges which can be affected in finding the IMT are: (a) how well the ultrasound probe is gripped with the neck of a patient to scan the carotids; (b) how well the ultrasound gel is being applied; (c) the orientation of the probe; (d) demographics of the patient; (e) skills of the sonographer or vascular surgeon; (f) gaps in the intensity distribution along the adventitia walls of the carotid ultrasound images; (g) shadows cones in the adventitia borders due the presence of calcium deposits; (h) threshold chosen for finding the peaks corresponding to the LI and MA points for each signal orthogonal to the lumen; (i) variability in the lumen region; (j) variability in the geometric shapes of the carotid scans such as convex, concave, up-hill, down-hill, and finally, (k) handing the large databases to process large number of images.

Thus, a system and method for fast, reliable and automated method for IMT measurements is needed.

BRIEF DESCRIPTION OF THE DRAWINGS

FIG. 3 shows that if there is a calcium cone shadow computes the IMT by correcting the IMT so-called the shadow correction. Shadow corrected processes estimate the IMT values under calcium shadow projection, while these processes simply run if there is no calcium shadow cone.

FIG. 26 is a processing flow diagram illustrating an example embodiment of a computer-implemented system and method for fast, reliable, and automated embodiments for using a validation embedded multi-resolution edge flow approach to vascular ultrasound for intima-media thickness (IMT) measurement as described herein.

DETAILED DESCRIPTION

Figure 1A:
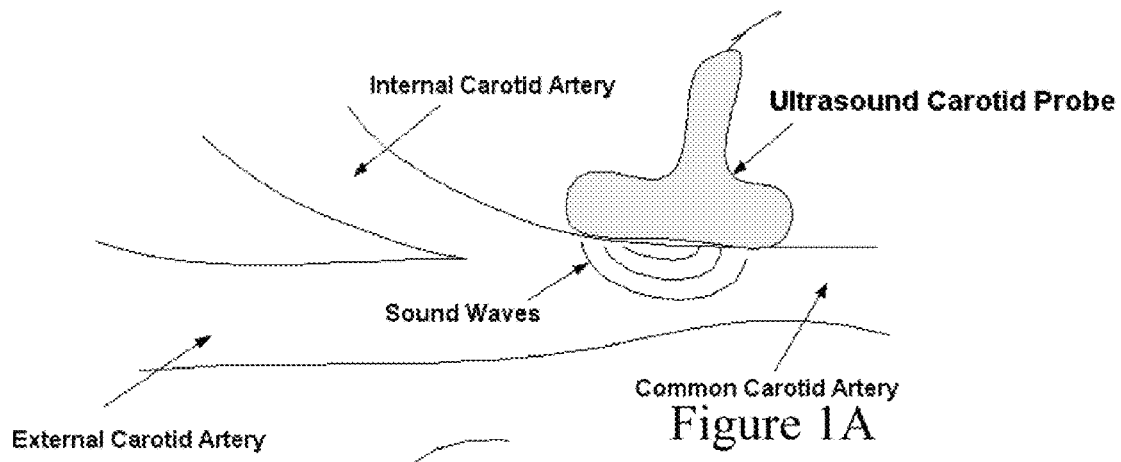
FIG. 1A shows the ultrasound scanning of the Carotid Artery. This can be a common carotid artery (CCA) or an internal carotid artery (ICA).

Recognition of the carotid artery consists of finding a regional layer close to the carotid artery and possibly all along the carotid artery in the image frame. This recognition process must ensure that we are able to distinguish the carotid artery layer from other veins such as jugular vein (JV). We modeled the carotid artery recognition process by taking the hypothesis that carotid artery's far wall adventitia is the brightest in the ultrasound scan frame; hence if we can automatically find this layer, then segmentation process of the far wall would be more systematic and channeled. Since the scanning process of carotid artery yields varying geometries of the carotid artery in the ultrasound scans, one has to ensure that the recognition process is able to handle various geometric shapes of the carotid arteries in the images. The process of location of far adventitia bright layer in the image frame can be supported by the fact that it is very close to lumen region, which carries the blood to the brain. Taking these two properties of the carotid artery ultrasound scan, this patent application has modeled the recognition process as a tubular model where the walls are considered as bright layers of the scan which can be picked up by the high intensity edge detector. Our edge model must keep in mind that the far adventitia layers are about a millimeter thick (which is about 16 pixels in image frame). Thus one would need to find an edge operator (preferably Gaussian in nature) which has an ability to have a width (scale) region of as wide as 8 pixels in the image frame. We have modeled this width to be the scale factor of the Gaussian kernel, where the scale is the standard deviation of the edge operator. The ability of finding this edge can be obtained by convolving the image region with a derivative of the Gaussian Kernel having a scale factor as rationalized in the edge model. Thus the whole idea of finding automatically the far adventitia border can be brought in the frame work of scale-space, where the image is convolved with first or higher order derivatives of Gaussian Kernel with known scale (s). While the scale-space model is fancy in itself, one must remember that it is very important to have the scale nearly fitting the far adventitia border region. Since the image frame is large enough to have a wider scale, we therefore have further adapted an approach where the scale-space model will behave consistent with respect to the image size. This requires that image be down sampled to half before the scale-space model can be adapted. Thus one can call this framework to be more like a multi-resolution thereby using the correct scale for capturing the edges of the far adventitia layers. Thus our architecture for stage I is the recognition of the far adventitia location in the grayscale image of the carotid artery using multi-resolution approach in scale-space framework.

In the following description, for purposes of explanation, numerous specific details are set forth in order to provide a thorough understanding of the various embodiments. It will be evident, however, to one of ordinary skill in the art that the various embodiments may be practiced without these specific details.

This patent application discloses various embodiments of a computer-implemented system and method for fast, reliable, and automated embodiments for vascular ultrasound for validation embedded LIMA segmentation and intima-media thickness (IMT) measurement. In particular, this patent application discloses various embodiments of a computer-implemented system and method for intima-media thickness (IMT) measurements using a validation embedded segmentation method. The various embodiments described herein also include the features described in more detail below.

Coarse to Fine Resolution Processing: Previous art has focused on methods for either classification of media layer or finding the MA edges in the manual designated Region of Interest (ROI). Since it is manual ROI, it is time consuming and non-practical for clinical applications, we have developed a new method which is fast, accurate, reliable and very practical for IMT measurement for carotids, brachial, femoral and aortic blood vessels. Since the manual methods are time consuming and requires a lot of training, this applications is a two step stage process: (a) automated validation embedded artery recognition and (b) automated calibration which finds the LIMA borders more accurately. The automated recognition process is hard given the Jugular vein in the neighborhood. Our concept is to recognize the artery in a smaller image with a high speed (so-called coarse resolution) and recognize the artery out. The spotted artery can then be seen in the fine resolution or high resolution. This will allow processing the pixels in the correct region of interest. The statistics of the neighboring pixels will not affect the region of interest, which is where the accurate LIMA borders need to be determined. Normally, arteries are about 10 mm wide while the media thickness is about 1 mm wide. It is also known from our experience that the image resolution is about 15-17 pixel per mm. If we can bring the original resolution to a coarse resolution by one step down sample, we can bring the media layer to about 8 pixels per mm. Further, if this coarse resolution is down sampled by another half, then one can bring the image resolution from 8 pixels/mm to 4 pixels/mm. Thus, if the coarse resolution of the arterial ultrasound vessels has a medial thickness of 4 pixels/mm, one can easily detect such edges by convolving the higher order derivatives of Gaussian kernel with the coarse resolution image. Thus, a new concept here is to automatically detect the arterial wall edges by down sampling the image and convolving the coarse images to higher order derivatives of Gaussian kernels. This allows the media layer to be automatically determined. Such an approach for automated media layer detection from fine to coarse resolution will further improve the region of interest determination. The art of changing the fine to coarse resolution has been popular in computer vision sciences. There are several methods available to converting the image from high resolution to coarse resolution. One of them is wavelet-based method where wavelets are being applied for down sampling the image to half. Another method can be hierarchical down sampling method using Peter Burt's algorithm. Thus the first advantage of the current system is automated recognition of the artery at coarse resolution and then using the MA border for visualization and recognition at the fine resolution (up-sampled resolution). This scheme has several advantages to it:

(1) Robustness and Accurate Wall Capture: it is very robust because the higher order derivative kernels are very good in capturing the vessel walls (see, A Review on MR Vascular Image Processing Algorithms: Acquisition and Pre-filtering: Part I, Suri et al., IEEE TRANSACTIONS ON INFORMATION TECHNOLOGY IN BIOMEDICINE, VOL. 6, NO. 4, pp. 324-337, December 2002; and A Review on MR Vascular Image Processing: Skeleton Versus Nonskeleton Approaches: Part II, Suri et al., *IEEE TRANSACTIONS ON INFORMATION TECHNOLOGY IN BIOMEDICINE*, VOL. 6, NO. 4, December 2002).

(2) Scale-space Method for Automated Recognition: Since the scale of the derivative Gaussian Kernels are determined using the anatomic information of the artery along with the multi-resolution framework, the system is robust to find the far adventitia borders.

(3) Validation Embedded Segmentation of Vascular IMT estimation: Here the recognition of artery has been validated by the anatomic information during the segmentation process. Since lumen is the anatomic information which is blood carrier to brain and is next to the far adventitia borders, which needs to be located, therefore, this patent application uses the anatomic information (lumen) to ensure that the far adventitia borders are robustly computed along the CCA/ICA, and do not penetrate the lumen region or near wall region. This adds robustness to our automated recognition and IMT measurement system.

(4) Faster than the conventional processing: Since the recognition is strategized at coarse level down sampled twice from its original size of the image, it is therefore processing $1/4^{th}$ the number of pixels for automated recognition of the media layer. This improves the speed of the system.

(5) Independent of Orientation of the vascular scan: Another major advantage to the system is that these Gaussian kernels are independent of the orientation of the blood vessels in the image. Since the ultrasound vascular scans do not always have the vessel orientation horizontal with respect bottom edge of the image, manual methods can pose a further challenge towards the region of interest estimation.

(6) Guiding Method for the calibration System: Since the recognition is followed by the calibration process, the calibration system becomes very robust since the calibration processing is done in the region of interest determined by the automated validation embedded recognition system. Thus the calibration system adds the value determined by the automated recognition system for vascular ultrasound such as IMT measurement for carotid, femoral, aortic and brachial. Such a combination where the calibration system is guided by the automated recognition system helps in mass processing of huge database processing.

(7) Running the Mass IMT system for Clinical Analysis: Since the recognition is automated followed by the calibration system, the largest value such a system would deliver will be in its real time use for analysis of IMT measurement on a large databases. Running clinical databases on still images would be even more beneficial because such a system would be completely automated in terms of arterial recognition and IMT measurement.

(8) Applications: Since the ultrasound probes use almost the same frequency of operation for scanning the vascular arteries such as carotid, femoral, brachial and aortic, it is thus possible to use such a system for these blood vessels.

In the prior art, we have seen that the speckle reduction has been used for removing speckles in the ultrasound images. Though speckle reduction is common in ultrasound imaging, but the way speckle reduction is used here is very conservative. The idea here is to find out where the LIMA borders are using automated recognition system and then apply the local statistical speckle reduction filter in specific set of pixels which come under the LIMA band or media layer. Such a strategy allows multiple advantages:

(1) Avoiding Large Computation Times on Speckle Reduction: The computation time for speckle reduction is not wasted in such a strategy, unlike conventional methods, where the speckle reduction is part of the whole streamline flow and is being run on the whole image.

(2) Speckle Reduction is implemented on the original raw intensity in the region estimated at a Coarse Resolution: Second, the speckle reduction filter is run in the automated recognized region (MA borders) which is actually applied on the original image rather than on the coarse image. This way the original speckles are removed preserving the intensities of high gradient structures like LI and MA peaks. This is very important because the calibration system acts on these speckle reduction region of interest.

(3) Guidance to the calibration System: The calibration system is guided by the speckle reduction filter which is optimized for the region of interest.

Extracting LIMA borders in presence of Calcium Shadow: Calcium is an important component of the media layer. It is not exactly known how the calcium is formed, but it is said that calcium accumulates in the plaques. During the beginning of Atherosclerosis disease, the arterial wall creates a chemical signal that causes a certain type of WBC (white blood cells) such as monocytes and T cells that attaches the arterial wall. These cells then move into the wall of the artery. These T cells or monocyles are then transformed into foam cells, which collect cholesterol and other fatty materials and trigger the growth of the muscle cells (which are smooth in nature) in the artery. Over time, it is these fat-laden foam cells that accumulate into plaque covered with a fibrous cap. Over time, the calcium accumulates in the plaque. Often times, the calcium is seen in the near wall (proximal wall) of the carotid artery or aortic arteries. This causes the shadow cone formation in the distal wall (far wall). As a result the LI boundaries are over computed from its actual layer. The shadow causes the LI lining over the actual. LI boundary. As a result, the LI-MA distances are over computed in the shadow zone. Because of this, the IMT formation is over computed in these cases.

This application particularly takes care of IMT computation during the shadow cone formation. We will see how the actual LI boundaries, are recovered if calcium is present causing the shadow cone. As a result, the IMT computation has the following advantages when using shadow cones.

(1) Accurate IMT computation in real time when the calcium is present in the proximal wall (near wall) causing the shadow cone formation.

(2) The system allows computing the IMT in both cases: (a) when calcium is present and when calcium is not present.

BRIEF SUMMARY OF AN EXAMPLE EMBODIMENT

The completely automated technique we developed and named CAMES (or AtheroEdge™) consists of two steps: (i) the automated validation embedded recognition of the CA in the image frame, and (ii) the segmentation of the far carotid artery wall. The automatically traced LI and MA profiles are used to measure the IMT.

Cropping System: Preliminarily, the raw ultrasound image is automatically cropped in order to discard the surrounding black frame containing device headers and image/patient data (1). If the image came in DICOM format, we relied on the data contained in the specific field named SequenceOfUltrasoundRegions, which contains four sub-fields that mark the location of the image containing the ultrasound representation. These fields are named RegionLocation (their specific label is xmin, xmax, ymin and ymax) and they mark the horizontal and vertical extension of the image. The raw B-Mode image is then cropped in order to extract only the portion that contains the carotid morphology. Those skilled in the art of DICOM will know that if the image came in from other formats or if the DICOM tags were not fully formatted, one can adopt a gradient-based procedure. We computed the horizontal and vertical Sobel gradient of the image. The gradients repeat similar features for the entire rows/columns without the ultrasound data: they are zero at the beginning and at the end. Hence, the beginning of the image region containing the ultrasound data can be calculated as the first row/column with gradient different from zero. Similarly, the end of the ultrasound region is computed as the last non-zero row/column of the gradient.

Automatic Recognition of the CA: To automatically identify the CA in the image frame, we developed a novel and low-complexity procedure. Following sample steps are used for automatic CA recognition, starting with the automatically cropped image which constitutes the input of the procedure.

Downsampling. The image was first down-sampled by a factor of 2 (i.e., the number of rows and columns of the image was halved).

Speckle reduction. Speckle noise was attenuated by using a first-order statistics filter (named as lsmv by the authors (2, 3)), which gave the best performance in the specific case of carotid imaging. This filter is defined by the following equation:

$$J_{x,y} = \overline{I} + k_{x,y}(I_{x,y} - \overline{I}) \tag{1}$$

where, $I_{x,y}$ is the intensity of the noisy pixel, $\overline{I}$ is the mean intensity of a N×M pixel neighborhood and $k_{x,y}$ is a local statistic measure. The noise-free pixel is indicated by $J_{x,y}$. Loizou et al. (2) mathematically defined $$k_{x,y} = \frac{\sigma_I^2}{\overline{I}^2 \sigma_I^2 + \sigma_n^2},$$

where $\sigma_I^2$ represents the variance of the pixels in the neighborhood, and $\sigma_n^2$ the variance of the noise in the cropped image. An optimal neighborhood size was shown to be 7×7.

Higher order Gaussian derivative filter. The despeckled image was filtered by using a first order derivative of a Gaussian kernel filter. It is possible to observe how the CA walls become enhanced to white. The sigma parameter of the Gaussian derivative kernel was taken equal to 8 pixels, i.e. to the expected dimension of the IMT value. In fact, an average IMT value of say 1 mm corresponds to about 16 pixels in the original image scale and, consequently, to 8 pixels in the down-sampled scale.

$AD_F$ refinement using anatomic information and spike removal. The traced $AD_F$ profile could be characterized by spikes and false points identification. This could be due to several reasons such as variations in intensities, gaps in the media walls, presence of jugular vein, shadow effects or combination of these. This innovation, therefore introduced a validation protocol, which provides a check on the far adventitia ($AD_F$) profile ensuring that the location of carotid artery is at correct place and the segmentation edge is not very bumpy. This validation step refines the far adventitia ($AD_F$) profile and is done in two steps: (a) refinement using anatomic lumen and (b) spike removal.

Refinement by anatomic reference (Lumen). This check has been introduced to avoid error conditions of $AD_F$ curve protruding into the lumen vessel. Thus, the refinement step requires the identification of the lumen region automatically. We have modeled the lumen segmentation region as a classification process with two classes. Carotid characteristics can be thought of as a mixture model with varying intensity distributions. This is because (a) the pixels belonging to the vessel lumen are characterized by low mean intensity and low standard deviation; (b) pixels belonging to the adventitia layer of the carotid wall are characterized by high mean intensity and low standard deviation; and (c) all remaining pixels should have high mean intensity and high standard deviation. As a result of this distribution, we derived a bi-dimensional histogram (2DH) of the carotid image. For each pixel, we considered a 10×10 neighborhood of which we calculated the mean value and the standard deviation. The mean values and the standard deviations were normalized to 0 and 1 and were grouped into 50 classes each having an interval of 0.02. The 2DH was then a joint representation of the mean value and standard deviation of each pixel neighborhood. It is well established that pixels belonging to the lumen of the artery are usually classified into the first classes of this 2DH: expert sonographer manually traced the boundaries of the CCA lumen and observed the distribution of the lumen pixels on the 2DH. Overall results revealed that pixels of the lumen have a mean values classified in the first 4 classes and a standard deviation in the first 7 classes. We therefore consider a pixel as possibly belonging to the artery lumen if its neighborhood intensity is lower than 0.08 and if its neighborhood standard deviation is lower than 0.14. This method shows how the local statistic is effective in detecting image pixels that can be considered as belonging to the CCA lumen. The $AD_F$ points along the CA are considered one by one. For each $AD_F$ point:

1. We consider the sequence of the 30 pixels above it (i.e., the 30 pixels located above the $AD_F$ point, towards the top of the image, and, therefore, with lower row indexes).
2. The $AD_F$ point failed the lumen test, if the $AD_F$ point crosses the lumen region and has penetrated the lumen region by at least 30 pixels inside the lumen or more. These failed points must not belong to the $AD_F$ boundary. These $AD_F$ points which fail the lumen test are tagged as 0, while rest of the points are tagged as 1. All the $AD_F$ points that tagged as 0 are deleted from the $AD_F$ list.
3. The procedure is repeated for each $AD_F$ point along the CA artery.

Note that even though, the lumen anatomic information, which acts as a reference, provides a good test for catching a series of wrongly computed ADF boundary, it might slip from sudden bumps which may be due to the changes in grayscale intensity due presence of unusual high intensity in lumen region or a calcium deposit in the near wall causing a shadow in far wall region. This sudden spike can then be easily detected ahead using the spike detection method.

Spike detection and removal. We implemented an intelligent strategy for spike detection and removal. Basically, we compute the first order derivative of the $AD_F$ profile and check for values higher than 15 pixels. This value was chosen empirically by considering the image resolution. When working with images having approximate resolution of about 0.06 mm/pixel, an IMT value of 1 mm would be about 17 pixels. Therefore, a jump in the $AD_F$ profile of the same order of magnitude of the IMT value is clearly a spike and error condition. If the spike is at the very beginning of the image (first 10 columns) or at the end (last 10 columns), then the spiky point is simply deleted. Otherwise, all spikes are considered and either substituted by a neighborhood moving average or removed.

Far adventitia $AD_F$ automated tracing. Intensity profile for one column of the filtered image is then taken. The near and far walls clearly has intensity maxima saturated to the maximum value of 255. To automatically trace the profile of the far wall, we used a heuristic search applied to the intensity profile of each column. Starting from the bottom of the image (i.e. from the pixel with the higher row index), we searched for the first white region of at least 6 pixels of width. The deepest point of this region (i.e. the pixel with the higher row index) marked the position of the far adventitia ($AD_F$) layer on that column. The sequence of all the points of the columns constituted the overall $AD_F$ automatically generated tracing.

Up-sampling to Fine Resolution. The $AD_F$ profile is then up-sampled to the original scale and overlaid to the original image. At this stage, the carotid artery far wall is automatically located in the image frame and automated segmentation is made possible.

Calibration Phase (Stage-II, Type I): We built a region-of-interest (ROI) around the automatically traced ADF profile. The ROI had the same width of the ADF curve. The height was equal to 30 pixels (1.8 mm for images with 16.67 pixels/mm of density, and 1.875 mm for images with 16 pixels/mm of density): for each point of the ADF profile we considered as upper limit of the ROI the pixel with a row index of 30 pixels lower. Substantially, the bottom limit of the ROI was the ADF curve and the upper limit the ADF but shifted upwards of 30 pixels.

We used the Calibration operator as segmentation strategy. The Calibration operator is an edge detector with good accuracy and robustness to noise. It was proposed by Demi et al. (M. Demi, M. Patemi, and A. Benassi, "The first absolute central moment in low-level image processing," *Computer Vision and Image Understanding*, vol. 80, no. 1, pp. 57-87, October, 2004) and subsequently adapted to the segmentation of the carotid wall in ultrasound images by Faita et al. (F. Faita, V. Gemignani, E. Bianchini, C. Giannarelli, L. Ghiadoni, and M. Demi, "Real-time measurement system for evaluation of the carotid intima-media thickness with a robust edge operator," *J Ultrasound Med*. vol. 27, no. 9, pp. 1353-61, September, 2008). We adopted the implementation suggested by Faita et al.:

$$e(x, y) = \frac{1}{A_\theta} \int \int_\theta |I_1(x, y) - I_2(x - x', y - y')| \cdot G(x, y, \sigma_r) dx' dy' \quad (2)$$

where $I_1(x,y)=I(x,y) \otimes G(x,y,\sigma_1)$ and $I_2(x,y)=I(x,y) \otimes G(x,y,\sigma_2)$ are computed by low-pass filtering the input image $I(x,y)$ by a Gaussian kernel with standard deviations equal to $\sigma_1$ and $\sigma_2$, respectively. This low-pass filtering step is required in order to cope with images having low values of signal-to-noise. The third Gaussian kernel $G(x,y,\sigma_r)$ is regularization and weighting term. When computed in a homogeneous region, the Calibration Edge operator $e(x,y)$ is zero valued. When computed in presence of a gray level discontinuity, the value of $e(x,y)$ increases. In our study, we used $\sigma_1=\sigma_r=0.3$ mm and $\sigma_2$ equal to 0.6 mm. Such values were tuned accordingly to the images resolution, as suggested in previous work.

The LI and MA interfaces were then searched by relying on heuristic search. The LI and MA transitions originate two high-intensity peaks on the Calibration profile, which can be automatically marked. For each intensity profile (i.e. for each column of the ROI), we marked the position of the higher intensity local maximum. Let's MAX1 be the intensity of this local maximum. Then we searched for a second local intensity maximum with a height MAX2≥0.1 MAX1. We marked the position of this second local maximum. Then, we searched for a local minimum comprised between MAX1 and MAX2. If such minimum was found, then we assigned MAX1 and MAX2 to the LI and MA interfaces. The deepest maximum was assigned to MA, the uppermost to LI. The sequence of all the LI and MA points of each column produced the final segmentation of the far carotid wall.

Detailed Description of an Example Embodiment

In the following description, for purposes of explanation, numerous specific details are set forth in order to provide a thorough understanding of the various embodiments. It will be evident, however, to one of ordinary skill in the art that the various embodiments may be practiced without these specific details.

This patent application discloses a computer-based system and method for intima-media thickness (IMT) measurements in presence of calcium or absence of calcium in near (proximal) end of the arterial value. The embodiment is being designed for carotid, femoral, brachial and aortic arteries. IMT measurement is a very important risk marker of the Atherosclerosis disease. Typically, there are two ways to measure the arterial IMT's: (a) invasive methods and (b) non-invasive methods. In invasive methods, traditionally, intravascular ultrasound (IVUS) is used for measuring vessel wall thickness and plaque deposits where special catheters are inserted in the arteries to image them. Conventional ultrasound is used for measuring IMT non-invasively, such as from carotid, brachial, femoral and aortic arteries. The main advantages of non-invasive methods are: (i) low cost; (ii) convenience and comfort of the patient being examined; (iii) lack of need for any intravenous (IV) insertions or other body invasive methods (usually), and (iv) lack of any X-ray radiation; Ultrasound can be used repeatedly, over years, without compromising the patient's short or long term health status. Though conventional methods are generally suitable, conventional methods have certain problems related to accuracy and reliability.

The IMTs are normally 1 mm in thickness, which nearly corresponds to 15 pixels on the screen or display. IMT estimation having a value close to 1 mm is a very challenging task in ultrasound images due to large number of variabilities such as: poor contrast, orientation of the vessels, varying thickness, sudden fading of the contrast due to change in tissue density, presence of various plaque components in the intima wall such as lipids, calcium, hemmorage, etc. Under normal resolutions, a 1 mm thick media thickness is difficult to estimate using stand-alone image processing techniques. Over and above, the image processing algorithms face an even tighter challenge due to the presence of speckle distribution. The speckle distribution is different in nature from these interfaces. This is because of the structural information change between intima, media and adventitia layers of the vessel wall. As a result, the sound reflection from different cellular structures is different. The variability in tissue structure—all that happens in 1 mm of the vessel wall—brings fuzziness in the intensity distribution of the vessel wall. Under histology, media and adventitia walls are clearly visible and one can observe even their thicknesses. This 1 mm zone is hard to discern in a normal resolution image of 256× 256 pixels in a region of interest (ROI) or in a higher resolution image of 512×512 pixels in a region of interest (ROI). One needs a high resolution, image to process and identify the intensity gradient change in ultrasound images from lumen to intima and media to adventitia layers. The ultrasound image resolution may not be strong enough like MRI or computerized axial tomography (CAT or CT) images, which can be meaningful for soft tissue structural information display.

There are two ways to process and identify the intensity gradient change in ultrasound images from lumen to intima (LI) and media to adventitia (MA) layers: (a) have a vascular surgeon draw the LI/MA borders and compute the IMT image interactively, OR (b) have a computer determine the LI and MA borders along with IMT's. Case (a) is very subjective and introduces variability in the IMT estimation. IMT screenings are really part of the regular check-up for patients and millions of scans are done each day around the world. The manual handling of such a repetitive work flow of IMT screenings is tedious, error-prone and subject to lot of variability. Case (b) is difficult to implement, because it is difficult to identify the LI and MA borders with heavy speckle distribution and the inability of ultrasound physics to generate a clear image where the semi-automated or automated image processing methods are used for IMT estimation. Besides that, the calcium deposit in the near walls causes the shadow.

Figure 3:
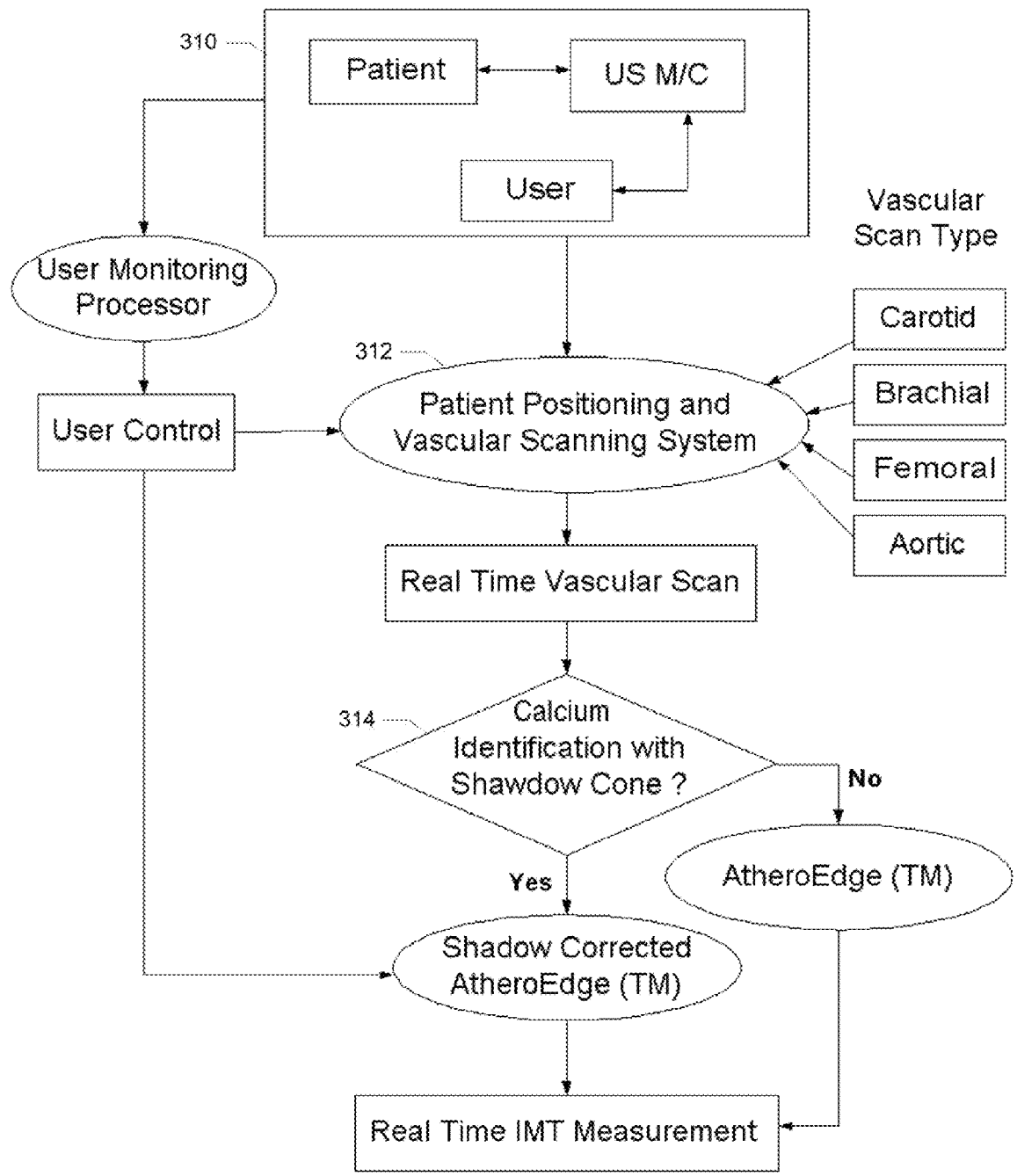
FIG. 3 shows the overall system of an example embodiment, which can be applied for computation of the IMT for any kind of vascular ultrasound data such as coming from Carotid, Brachial, Femoral and Aortic.

FIG. 3 shows the OPD (object process diagram) for the whole system. The top box shows the interacting system between ultrasound machine, patient and user. This invention is applicable to vascular ultrasound for carotid, brachial, arotic and femoral but not limited to these alone. For carotid, one can use the left and the right scan. When the patient comes in, the system is made to get ready for the ultrasound scan and IMT measurement. Patient is positioned optimally for the best scan and then Gel is applied before vascular scanning. The probe is then skin surfaced for the carotid scan as seen in the FIG. 1 (top). The first sub-system in FIG. 3 shows the patient positioning and vascular scanning system. The input to this block is vascular scan type: carotid, brachial, femoral and aortic, which means these four kinds of arteries, can be used for IMT measurement. The output to the system is the real time ultrasound vascular scan, normally DICOM in format. In the FIG. 3 is also shown that the user completely monitors the system all the time and is in user's control all the time. This allows for perfect synchronization of the patient interface with ultrasound and for the diagnostic IMT measurement system. Normally, the vascular screening is done by the vascular surgeon or a neuroradiologist or a sonographer or a cardiologist. They are trained to recognize any calcium present near the proximal wall zone. The diamond box shows if the calcium is present in arterial wall or not. The user such as neuroradiologist or sonographer or cardiologist or vascular surgeon uses his expertise to spot the calcium and its shadow in the proximal (near) end of the arterial wall. Those skilled in the art will note that even though the probe is used longitudinally in B-mode for scanning the arterial wall, one can change the orientation of the probe orthogonal to the blood flow and move the probe linearly along the carotids or brachial or femoral or aortic to get the transverse slices to see the extent (range) of the calcium.

Since the presence of the calcium in longitudinal B-mode scans causes the calcium cone in the ultrasound images, a different processing stage is required before AtheroEdge™ stand alone is applied for IMT measurement. AtheroEdge™ is made to activate if there is no calcium is present while AtheroEdge™ system with calcium correction is made to activate when calcium is spotted in the longitudinal or transverse B-mode images. The output of the AtheroEdge™ (with or without calcium system) is the real time IMT measurement. Note that the user completely monitors the system all the time and is in user's control all the time during the AtheroEdge™ system with calcium and AtheroEdge™ system without calcium.

Figure 1B:
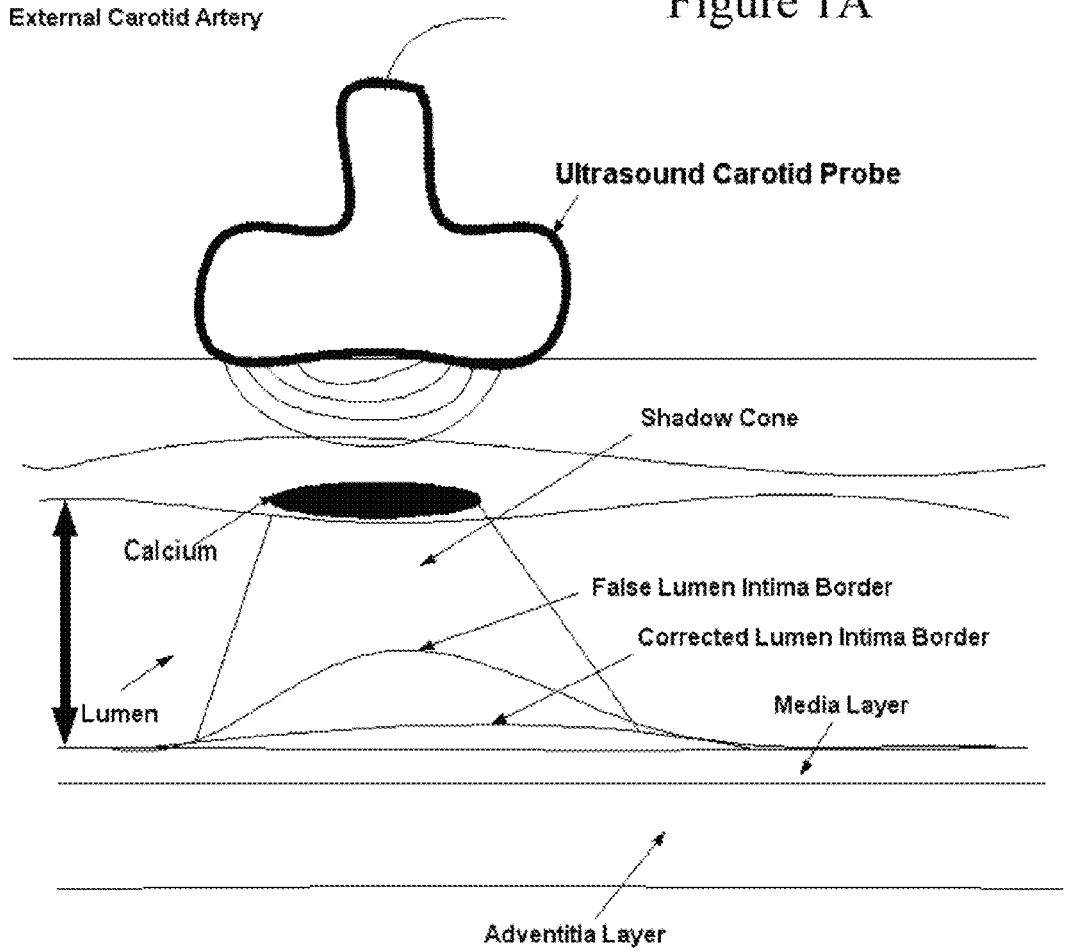
FIG. 1B shows the calcification seen in the proximal wall (near wall) of the ICA and its corresponding shadow.
Figure 2:
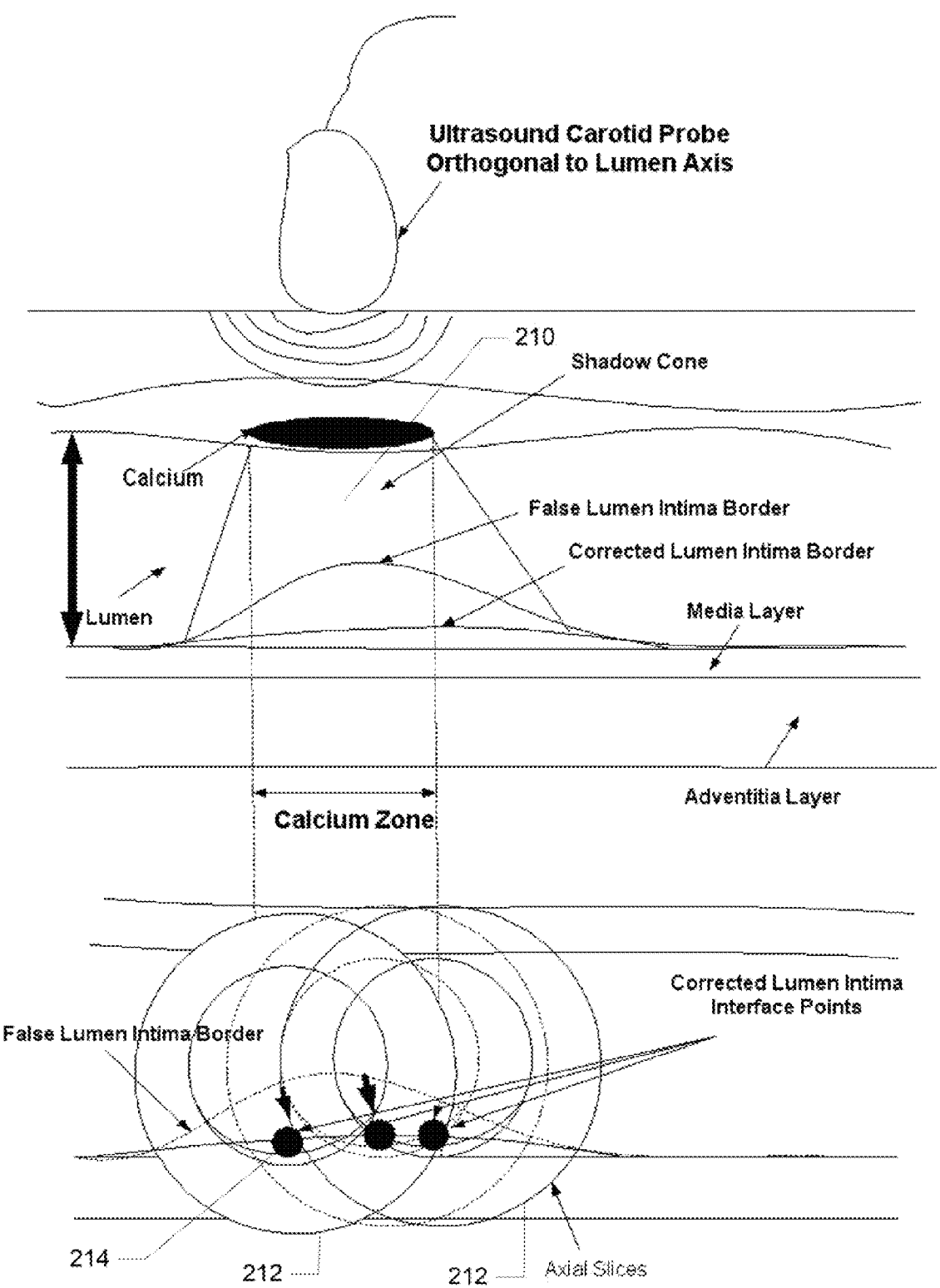
FIG. 2 shows the solution of the calcification issue, where the transverse slices are acquired instead of B-mode longitudinal images. These transverse slices are depicted as circular cross-sectional in the image.

FIG. 1 shows the diagrammatic view where calcium is present in the proximal wall. As can be seen in the figure a black region in the image in intima layer or media layer or in the lumen region but hanging from the intima layer. There are many variability of how the calcium can stick or hang in the proximal wall, but in every case, there will be a shadow caused when ultrasound is blocked by this calcium present in the arterial wall (see the details by Robin Steel et al., Origins of the edge shadowing artifact in medical ultrasound imaging, Ultrasound in Med. & Biol., Vol. 30, No. 9, pp. 1153-1162, 2004). It has been shown that calcification causes echogenity in the ultrasound image to be hypoechoic (darker) and covers the true reflection coming out of the media layer of the distal (far) borders. Okuda et al. showed these kind of hypoechoic zones in the ultrasound images due to the presence of calcium in the renal arteries (see, Okuda et al., Sonographic Features of Hepatic Artery Calcification in Chronic Renal Failure, Acta Radiologica 44, 2003. 151-153). IMT measurements in such cases can become difficult or challenging. This application just not finds the reliable and automated IMT measurements in ordinary arterial walls, but also in the presence of calcification. FIG. 2 shows the calcification of the proximal end of the wall and the shadow cone made by the calcification and projected onto the distal (far) end of the wall. Due to this as shown in the figure the LI borders are over calculated or wrongly calculated. Shown in the figure that using this patent application, we can correct the LI borders for the distal (far) end of the wall. This correction has to be applied in the region where calcification is present.

Thus we need a method, which can actually compute the IMT values if the user (cardiologist, neuroradiologist, vascular surgeon, sonographer) does not find the calcium shadows. We need a reliable, real time and accurate method for IMT measurement when there is no calcium present. Similarly, we need to find IMT when the calcium is present. When calcium is not present, the IMT computation uses AtheroEdge™ directly, but when calcium is present the system uses AtheroEdge™ in the non-calcium zones and correcting the LI border in the calcium zones and then interpolating with the LI border of the non-calcium zone thereby getting the complete and correct LI borders.

FIG. 2 shows the methodology used for correcting the LI borders when the calcium shadow cones are present. The method uses a combination of data acquisition and software method for correcting the LI borders. These two steps are done in real time while the probe is still sitting on the patient's artery. The combinational approach requires no change by the expert user (cardiologist, neuroradiologist, vascular surgeon, sonographer) who has been trained to use the probe on arterial anatomy. The holding method of using the probe still uses the same art by making the grip of four fingers and one thumb. The only change the user has to do is rotate his wrist 90 degree to the longitudinal axis. Once the calcium region is identified, the user (cardiologist, neuroradiologist, vascular surgeon, sonographer) rotates the orientation of the probe by rotating its wrist and taking the scans of the distal (far) wall. Since the probe is oriented orthogonal to the longitudinal axis of the arterial vessel, the images captures are axial or transverse in nature. The user then moves the probe with a reasonable speed linearly and while moving the probe, the transverse images are captured. The user can stop the linear movement of the probe as soon as the calcium region finishes.

These axial slices will show the vessel wall which is circular band in nature. The inner wall shows the lumen region and outer wall is the adventitia walls. Since we are interested in the distal (far) walls in longitudinal B-mode, we look for the vessel wall region in the distal area of the artery. Those skilled in the art of doing 3D ultrasound will notice that the lumen region is dark (black) and the vessel wall (relatively brighter than lumen region), hence the interface region is discernable between lumen and walls. This change in gradient information for the distal (far) wall for that particular slice will allow the user manually or semi-automatically or automatically to estimate the gradient change between the lumen and vessel wall for that orthogonal slice. FIG. 2 shows the circular wall boundaries of the lumen and media-adventitia layers in axial or transverse slices. The point of gradient change between the lumen and vessel wall corresponding to the longitudinal B-mode position of the probe, orthogonal to the arterial axis is the point, which corresponds to the LI border where calcium region was hit. This point is shown as a black circle in the FIG. 2. Those skilled in the art of boundary estimation can use off the shelf snake method or deformable method or edge detection method to find the lumen boundary in the transverse slice of the ultrasound arterial image. The above process of finding the point of intersection of the longitudinal B-mode position to the circular vessel wall in the transverse image is repeated for all the transverse slices where calcium region is identified. The information extracted for the shadow region is stored to be reused because that is the partial information on the LI border. The rest of the information will be extracted from AtheroEdge™ using the longitudinal B-mode vascular ultrasound image.

Figure 4:
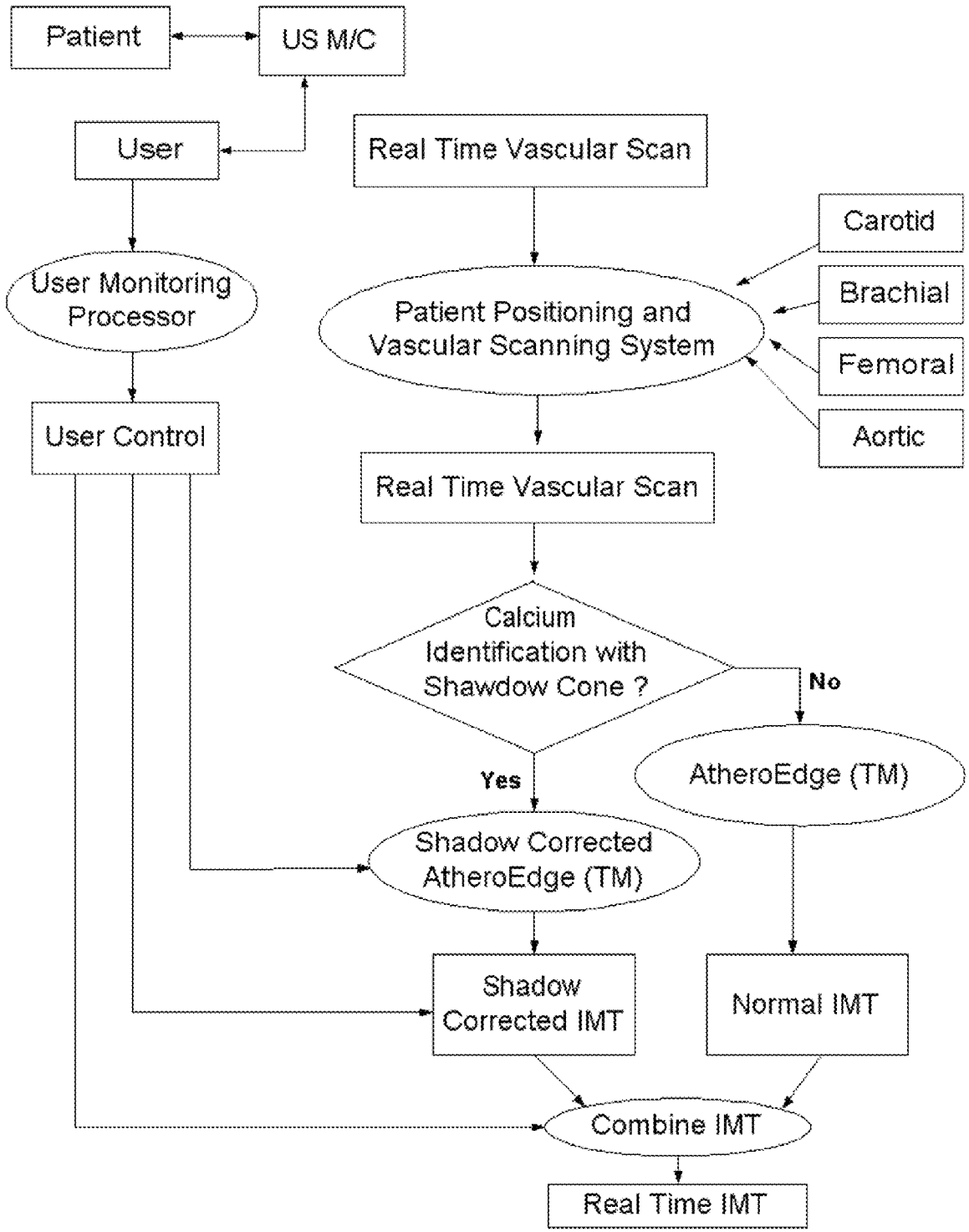
FIG. 4 shows the IMT values are combined with and without shadow cones. If there are no shadow cones (or calcium present), then the processes simply compute the real time IMT.

FIG. 4 actually shows the system which helps in combining the corrected LI boundary information from the calcium shadow zone (shadow corrected AtheroEdge™) and LI boundary information for the non-calcium shadow zone. This will lead to the formation of the full LI boundary and MA boundary leading to the distance measurement called IMT. This can be seen in the FIG. 4. During the complete process, we must ensure that user in full control as a fall back system should the automated system encounters a challenge, there by changing to the semi-automated system. If the user (cardiologist, neuroradiologist, vascular surgeon, sonographer) does not encounter the calcium shadow, then, the plain automated AtheroEdge™ will run for the IMT measurement.

Figure 5:
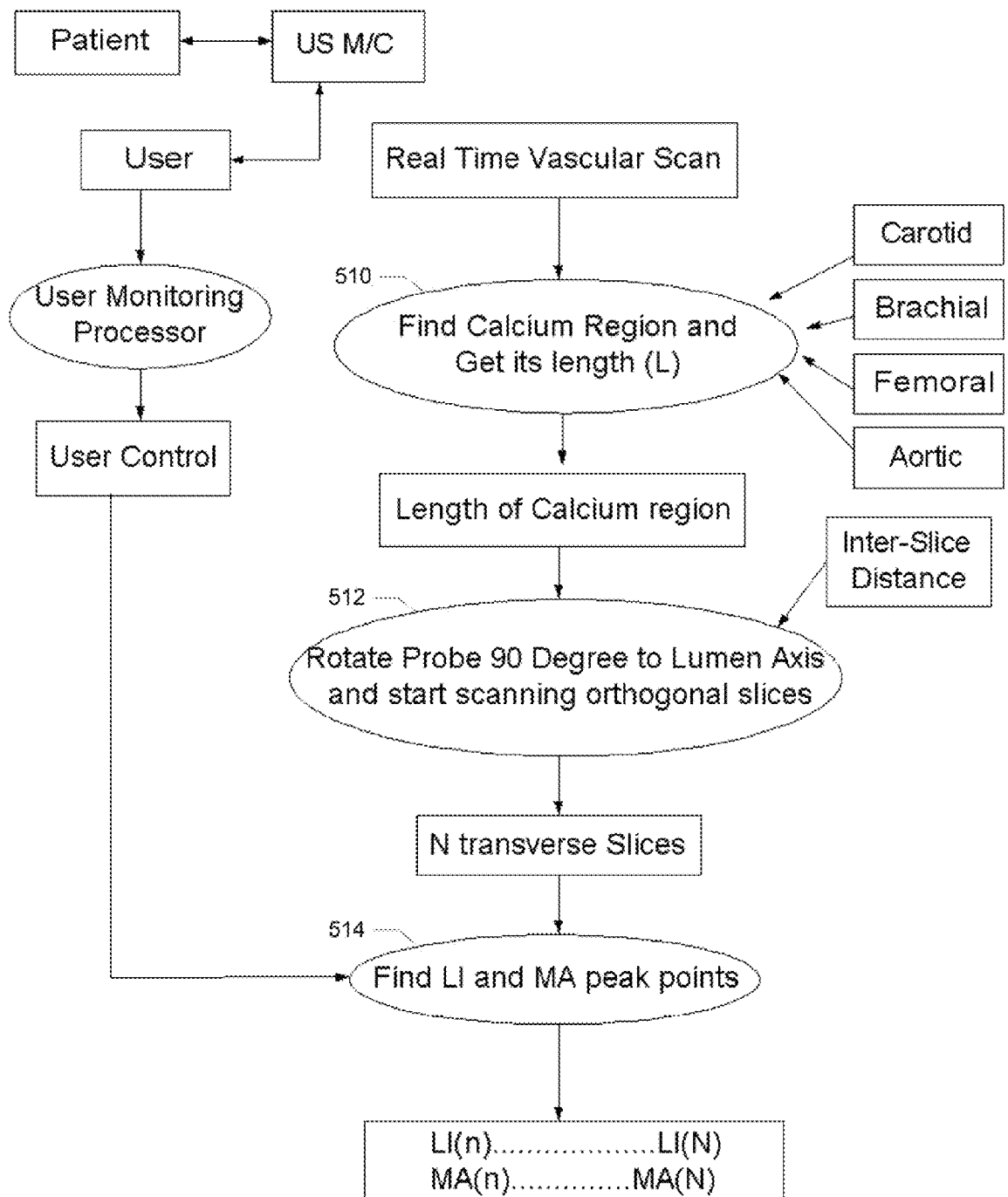
FIG. 5 shows data acquisition when the calcium is found in the proximal wall of the CCA/ICA during the ultrasound scans. The figure shows how the calcium zone is estimated in the proximal wall, then, how the probe orientation is changed to collect the transverse slices in the calcium zone. Finally, the figure shows how the lumen-intima and media-adventitia (LIMA) points are determined in the transverse slices.

FIG. 5 shows how the system for computing the LI and MA boundaries in the calcium shadow zone, which is connected to the FIG. 2. The main components are the length of calcium zone estimation, acquiring the N transverse slices and then estimating the LI boundary points corresponding to the shadow zone. Those skilled in the art of 3D ultrasound acquisition will notice that the inter-slice distance is important during the scanning process. In our methodology, it is not very critical information as we are only interested in limited number of points corresponding to the calcium zone.

Figure 6:
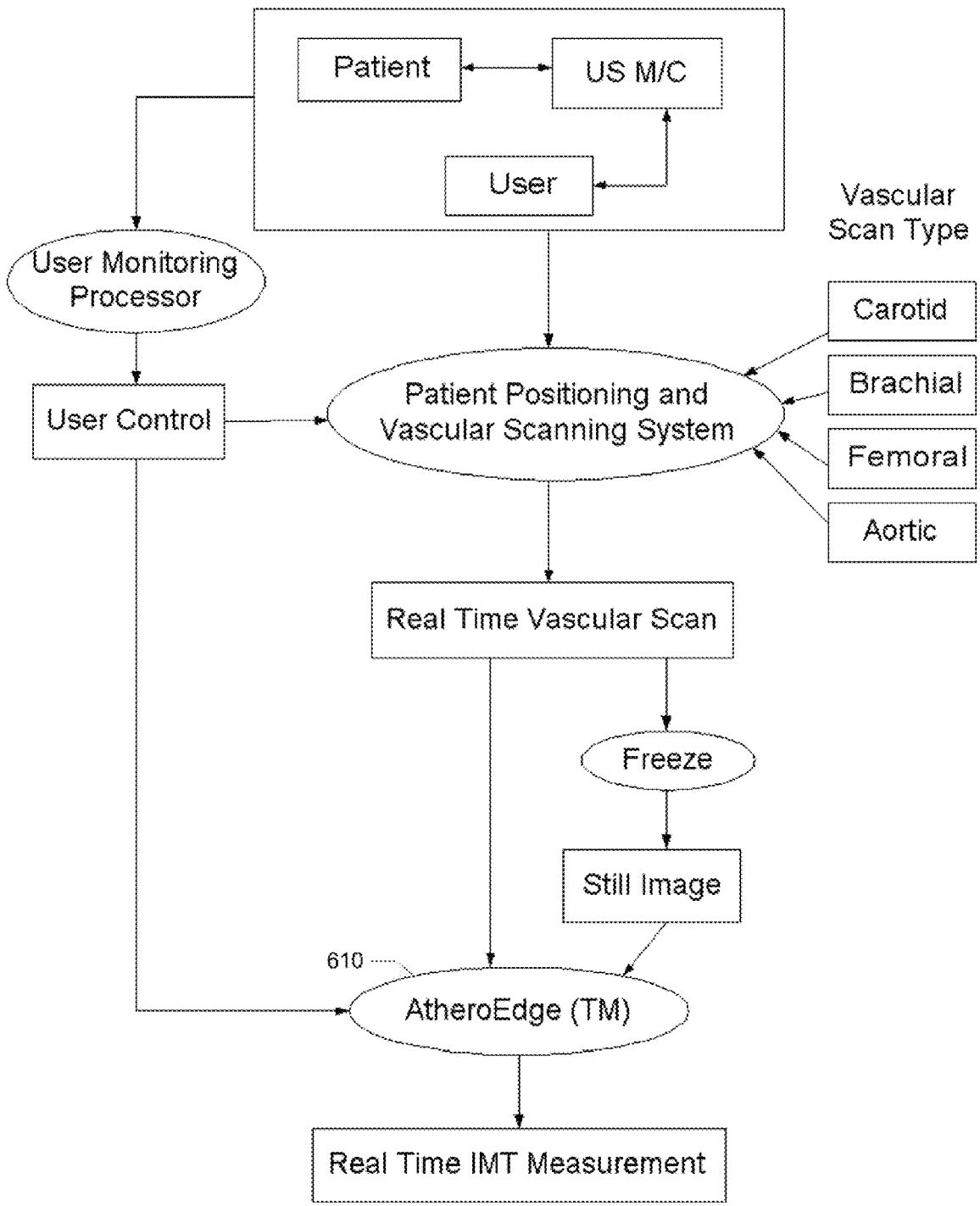
FIG. 6 shows how the system of various embodiments works given the still image of the B-mode longitudinal image of carotid or how the system of various embodiments works given the real time image of the B-mode longitudinal image of the carotid artery.

FIG. 6 shows the system where the AtheroEdge™ is being used in normal cases where there is no calcium shadow. The system shows how the ultrasound vascular image is acquired using the longitudinal B-mode process. The input to the system also shows that this process can take any of the four arteries: carotid, brachial, femoral and arotic. The system has ability to freeze the image as a still image, on which the IMT will be computed. User continuously monitors the process at all stages during the operation. User has control on the AtheroEdge™ software system, ultrasound machine, ultrasound probe, patient and the graphical user interface. The still image can be saved on the hard drive or CD drive. The still image can then also be transferred to an independent computer and AtheroEdge™ can be run on that system as well. At the same time AtheroEdge™ can run real time while the patient is in the vascular screening room.

Figure 7:
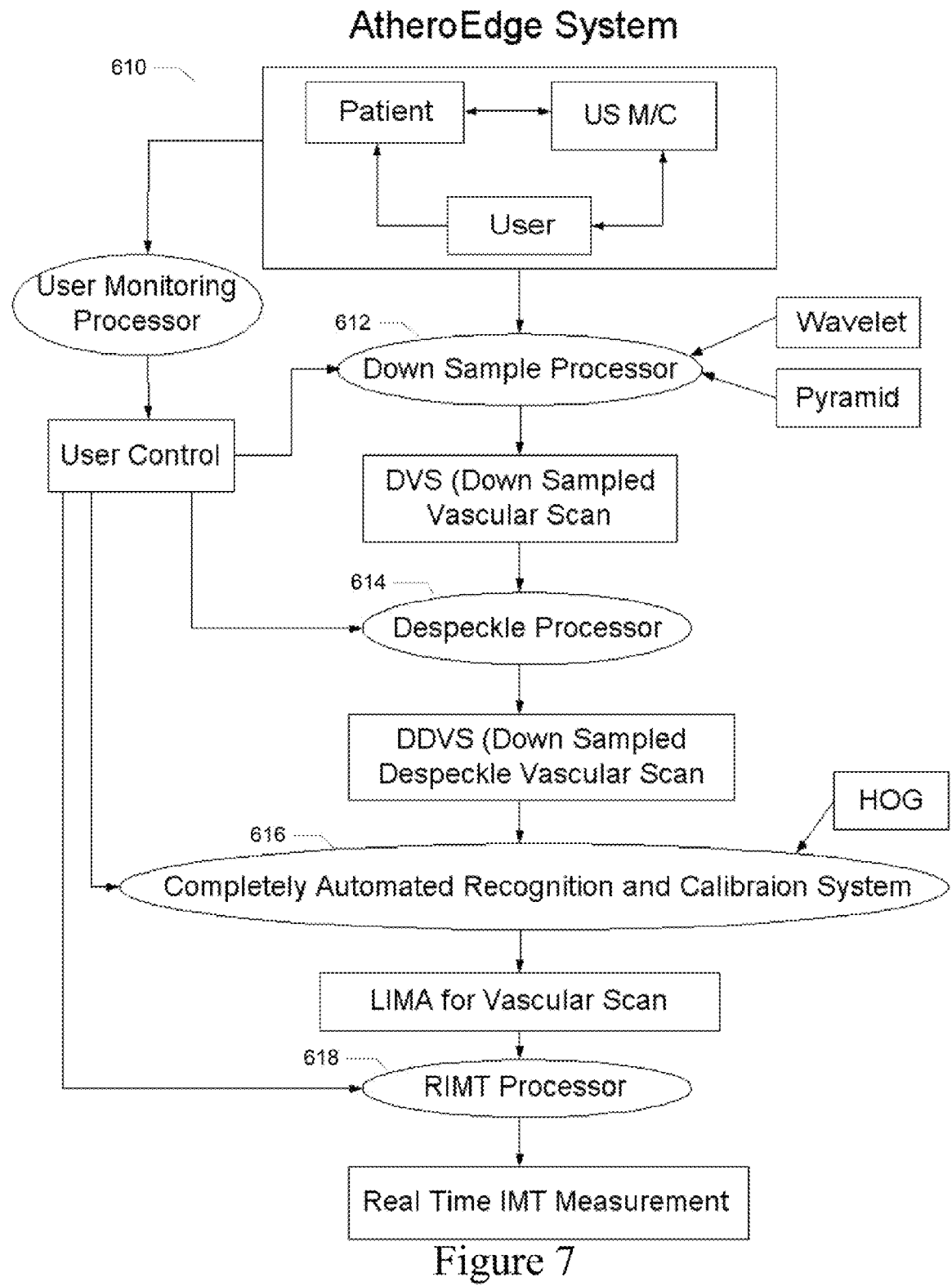
FIG. 7 shows the design of the system of various embodiments, which includes the following sub-systems: (a) down sample processor; (b) despeckles processor; (c) completely automated recognition and validation system (d) calibration system; and (e) Real-time IMT (RIMT) processor.

FIG. 7 shows the AtheroEdge™ system where the main components of the system are: (a) Multi-resolution Image. Processor; (b) De-speckle Processor; (c) Recognition, Validation Processor and Calibration Processor and (d) RIMT Processor.

Figure 8:
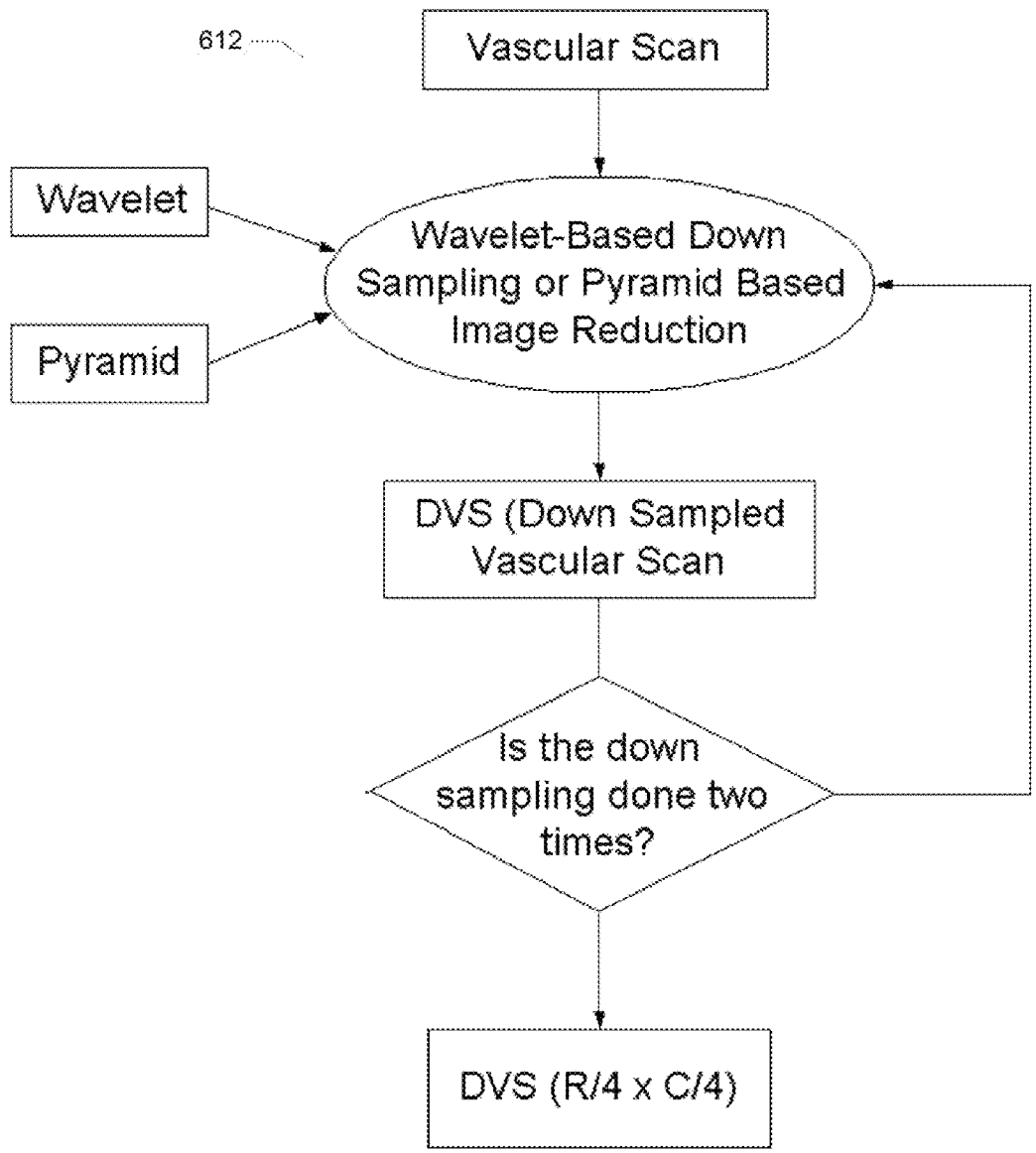
FIG. 8 shows, the image reduction processor based on wavelet transform or pyramid filter, which can down sample the image two steps down.

Multi-resolution image processing yields the DSVS (down sampled vascular scan) image. FIG. 8 shows the down sampling or fine to coarse resolution system. One of the four systems can be used for fine to coarse sampling. The role of the multi-resolution process is to convert the image from fine resolution to coarse resolution. Those skilled in the art of down sampling any use off the shelf down sampling methods. One of the very good down samplers are Lanczos interpolation. This is based on the sinc function which can be given mathematically as $$\mathrm{sinc}(x) = \frac{\sin(\pi x)}{\pi x}.$$

Since the sinc function never goes to zero, practical filter can be implemented by taking the sinc function and multiplying it by a "window", such as Hamming and Hann, giving an overall filter with finite size. We can define the Lanczos window as a sine function scaled to be wider, and truncated to zero outside of the main lobe. Therefore, Lanczos filter is a sine function multiplied by a Lanczos window. Three lobed. Lanczos filter can be defined as $$Lanczos3(x) = \begin{cases} \dfrac{\sin(\pi x)\sin\left(\pi \dfrac{x}{3}\right)}{\pi x \cdot \pi \dfrac{x}{3}}, & \text{if } |x| \le 3 \\ 0, & \text{if } |x| > 3 \end{cases}$$

Although Lanczos interpolation is slower than other approaches, it can obtain the best interpolation results because Lanczos method attempts to reconstruct the image by using a series of overlapping sine waves to produce what's called a "best fit" curve. Those skilled in the art of down sample can also use Wavelet transform filters as they are very useful for multi-resolution analysis. The orthogonal wavelet transform of a signal f can be formulated by $$f(t) = \sum_{k \in z} c_j(k)\varphi_{J,k}(t) + \sum_{J=t}^{J} \sum_{k \in Z} d_j(k)\varphi_{j,k}(t)$$

where the $c_j(k)$ is the expansion coefficients and the $d_j(k)$ is the wavelet coefficients. The basis function $\phi_{j,k}(t)$ can be presented as $$\phi_{j,k}(t) = 2^{-j/2}\phi(2^{-j}t-k),$$

where k, j are translation and dilation of a wavelet function φ(t). Therefore, wavelet transforms can provide a smooth approximation of f(t) at scale J and a wavelet decomposition at per scales. For 2-D images, orthogonal wavelet transforms will decompose the original image into 4 different sub-band (LL, LH, HL and HH).

Bicubic interpolation can also be used as it will estimates the value at a given point in the destination image by an average of 16 pixels surrounding the closest corresponding pixel in the source image. Given a point (x,y) in the destination image and the point (l,k) (the definitions of l and k are same as the bilinear method) in the source image, the formulae of bicubic interpolation is $$f(x, y) = \sum_{m=l-1}^{l+2} \sum_{n=k-1}^{k+2} g(m, n) \cdot r(m - l - dx) \cdot (dy - n + k),$$

where the calculation of dx and dy are same as the bilinear method. The cubic weighting function r(x) is defined as $$r(x) = 1/6[p(x+2)^3 - 4p(x+1)^3 + 6p(x)^3 - 4p(x-1)^3],$$

where p(x) is $$p(x) = \begin{cases} x & x > 0 \\ 0 & x \leq 0 \end{cases}$$

Bicubic approach can achieve a better performance than the bilinear method because more neighboring points are included to calculate the interpolation value.

Bilinear interpolator can also be used as it is very simple to implement. Mathematically, it is given as: if g represents a source image and f represents a destination image, given a point (x,y) in f, the bilinear method can be presented as:

$$f(x, y) = (1 - dx) \cdot (1 - dy) \cdot g(l, k) + dx \cdot (1 - dy) \cdot g(l + 1, k) +$$
$$(1 - dx) \cdot dy \cdot g(l, k + 1) + dx \cdot dy \cdot g(l + 1, k + 1),$$

where $l = \lfloor x \rfloor$ and $k = \lfloor y \rfloor$, and the dx, dy are defined as dx=x−l and dy=y−k respectively. Bilinear interpolation is simple. However it can cause a small decrease in resolution and blurring because of the averaging effect.

Figure 9:
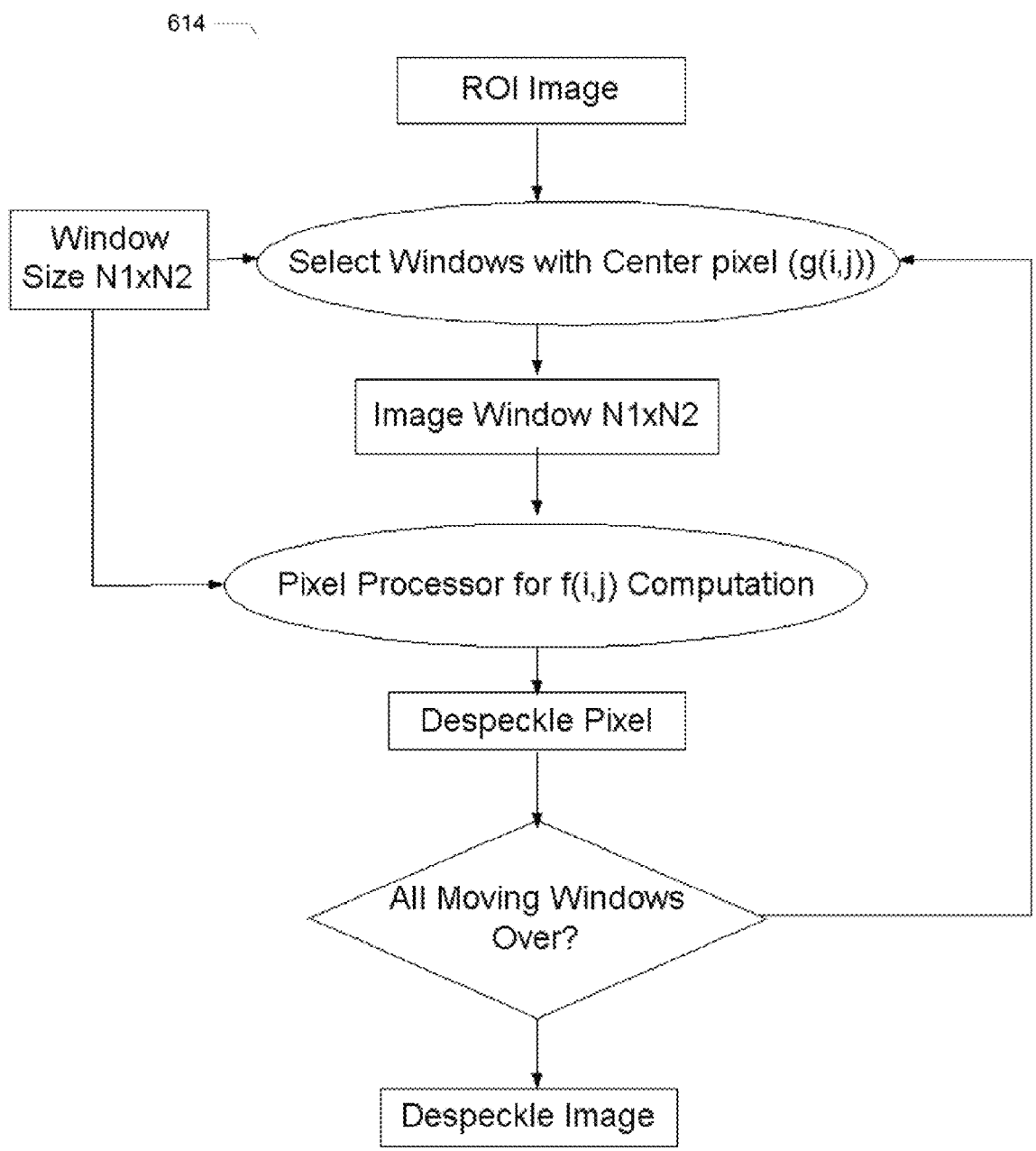
FIG. 9 shows the despeckle processor, which can remove the speckles in the ultrasound region of interest. A moving window method is used for generating the de-speckle filtering process.
Figure 10:
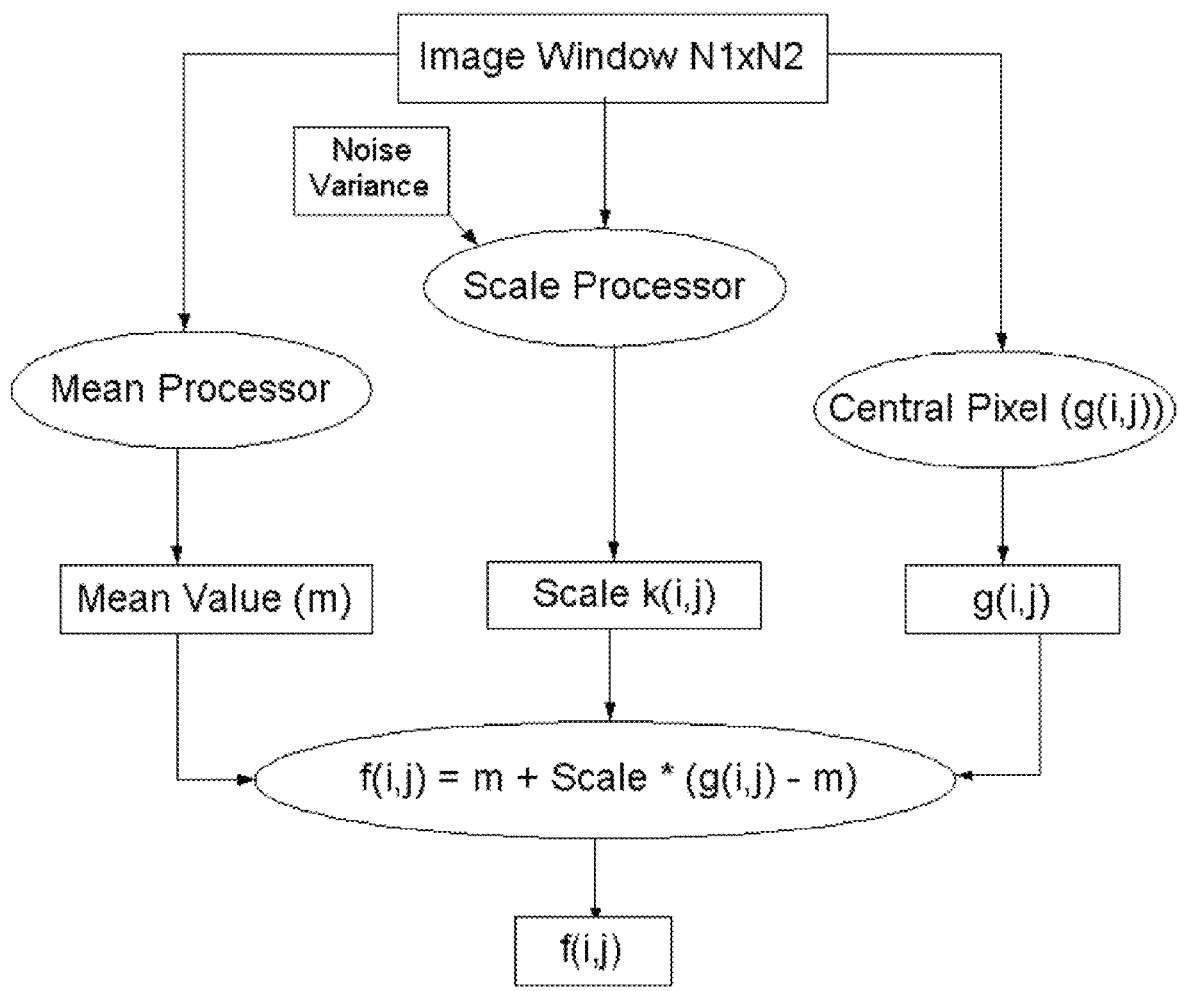
FIG. 10 shows the process for computing the de-speckle pixel and replacing the original noisy pixel. The process uses the scaling of the original pixel. The noise variance process is being used by the scale processor.
Figure 11:
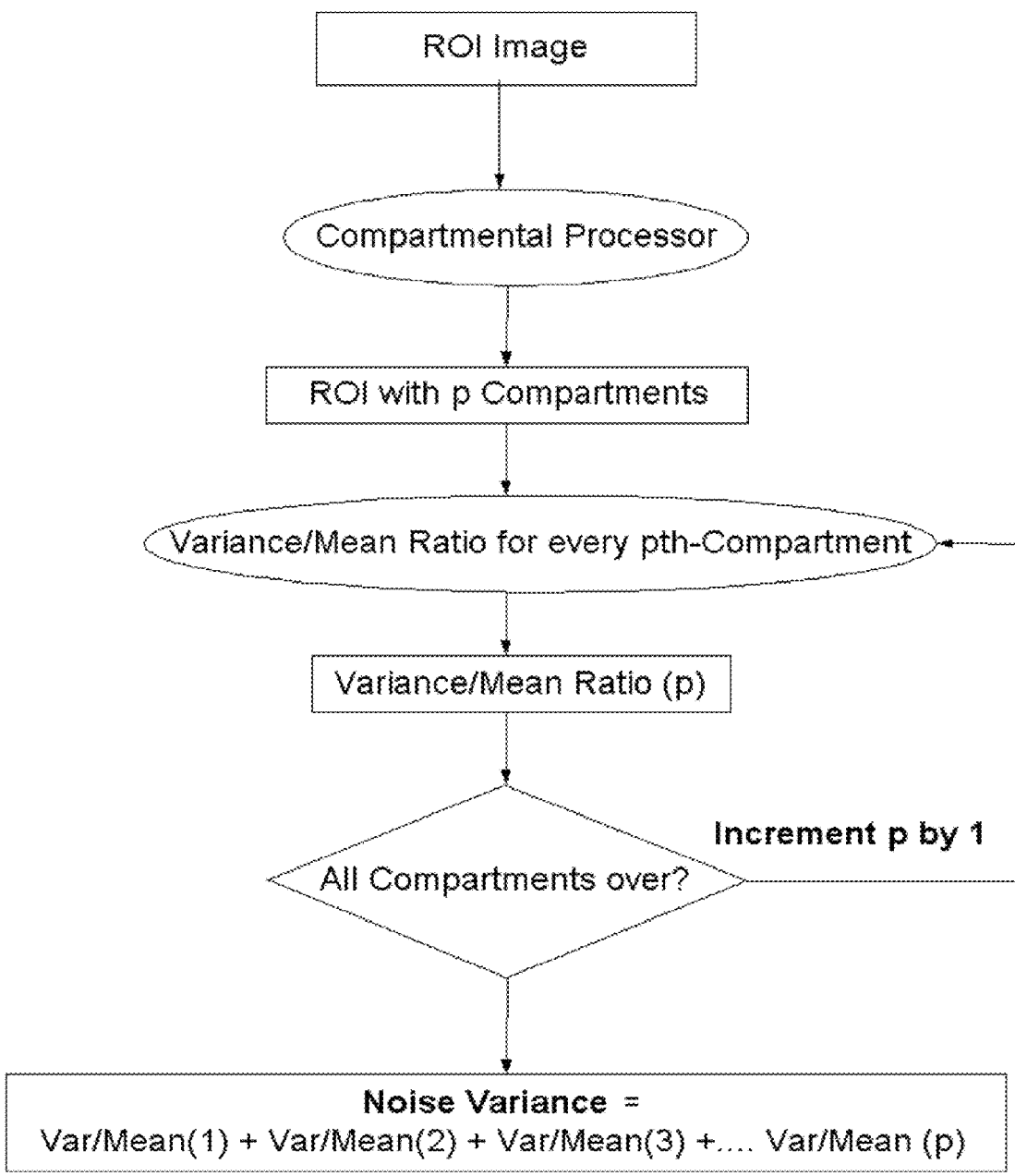
FIG. 11 shows the computation of the noise variance processor. The noise variance is computed by summing the variance to mean ratio for all the compartments of the ROI region. The figure shows if there are "p" compartments, then the noise variance is computed by summing the variance to mean ratio of each of the "p" compartments.

FIGS. 9, 10 and 11 deal with the de-speckle filtering; whose output is DDVS (Down sampled Despeckle Vascular Scan). Speckle noise was attenuated by using a first-order statistics filter, which gave the best performance in the specific case of carotid imaging. This filter is defined by the following equation:

$$J_{x,y} = \bar{I} + k_{x,y}(I_{x,y} - \bar{I}) \quad (1)$$

where, $I_{x,y}$ is the intensity of the noisy pixel, $\bar{I}$ is the mean intensity of a N×M pixel neighborhood and $k_{x,y}$ is a local statistic measure. The noise-free pixel is indicated by $J_{x,y}$. $k_{x,y}$ is mathematically defined $$k_{x,y} = \frac{\sigma_I^2}{\bar{I}^2 \sigma_I^2 + \sigma_n^2},$$

where $\sigma_I^2$ represents the variance of the pixels in the neighborhood, and $\sigma_n^2$ the variance of the noise in the cropped image. An optimal neighborhood size can be 7×7. Note that the despeckle filter is useful in removing the spurious peaks if any during the adventitia identification in subsequent steps.

Figure 12:
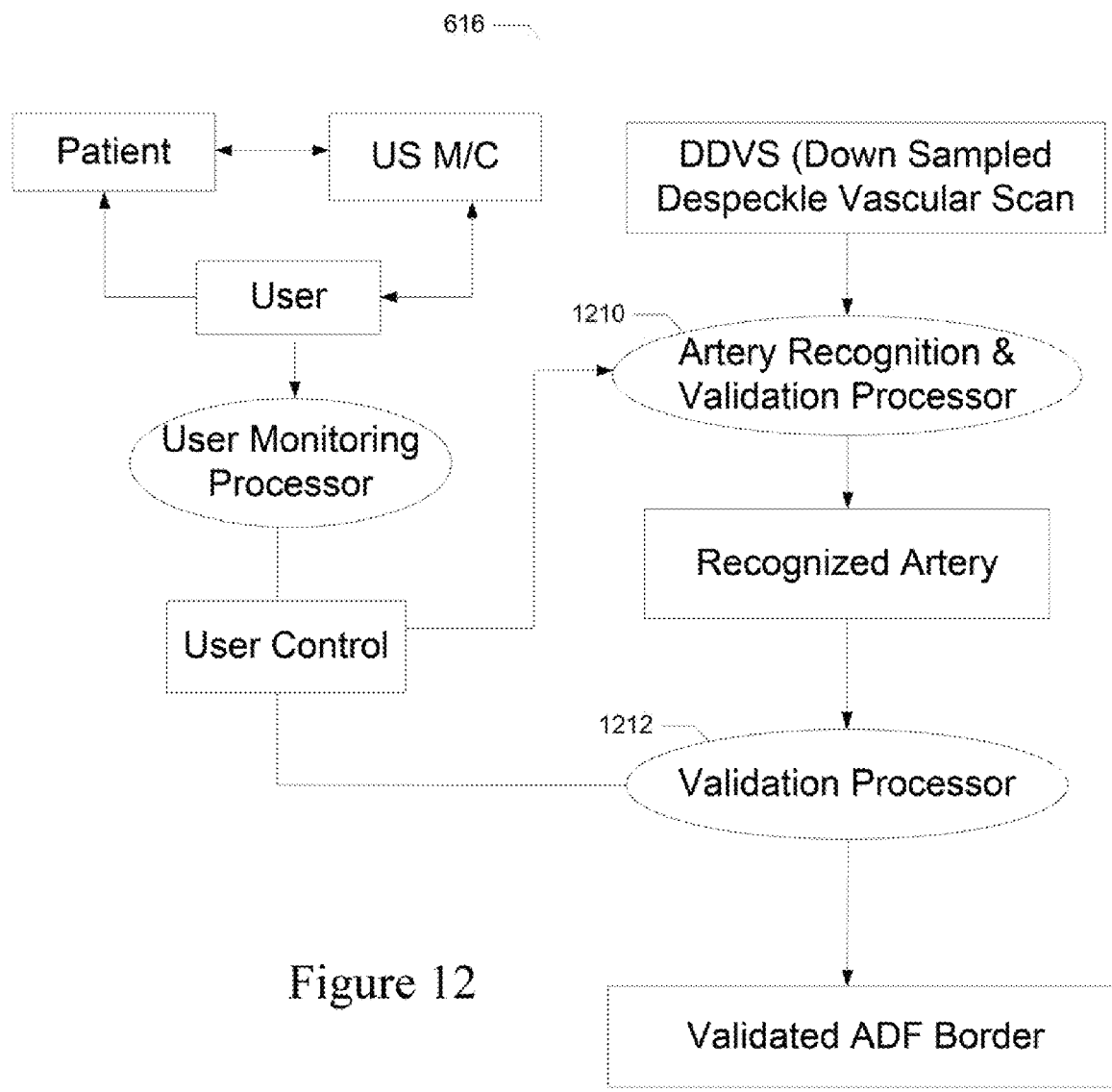
FIG. 12 shows the Artery Recognition and Validation Processor. It shows two phases: (a) recognition and validation processor for computing the LIMA borders after the automated recognition process and (b) Calibration phase is definite phase for any LIMA borders to be estimated along with the IMT values. Note calibration phases can be of two types: (i) based on first order moments or (ii) using edge flow methods using the intensity and textures.

FIG. 12 shows the last and the final stage is the recognition, validation and calibration system shown in the process called "Completely Automated Recognition and Calibration Processor". While the two stages are cascaded and shown to be different blocks, but it is transparent to the user. This means the software is cascading information from one block to another block without user interaction. The user still has full control and user monitoring processor is fully active and the user can interrupt the system any time.

Figure 13:
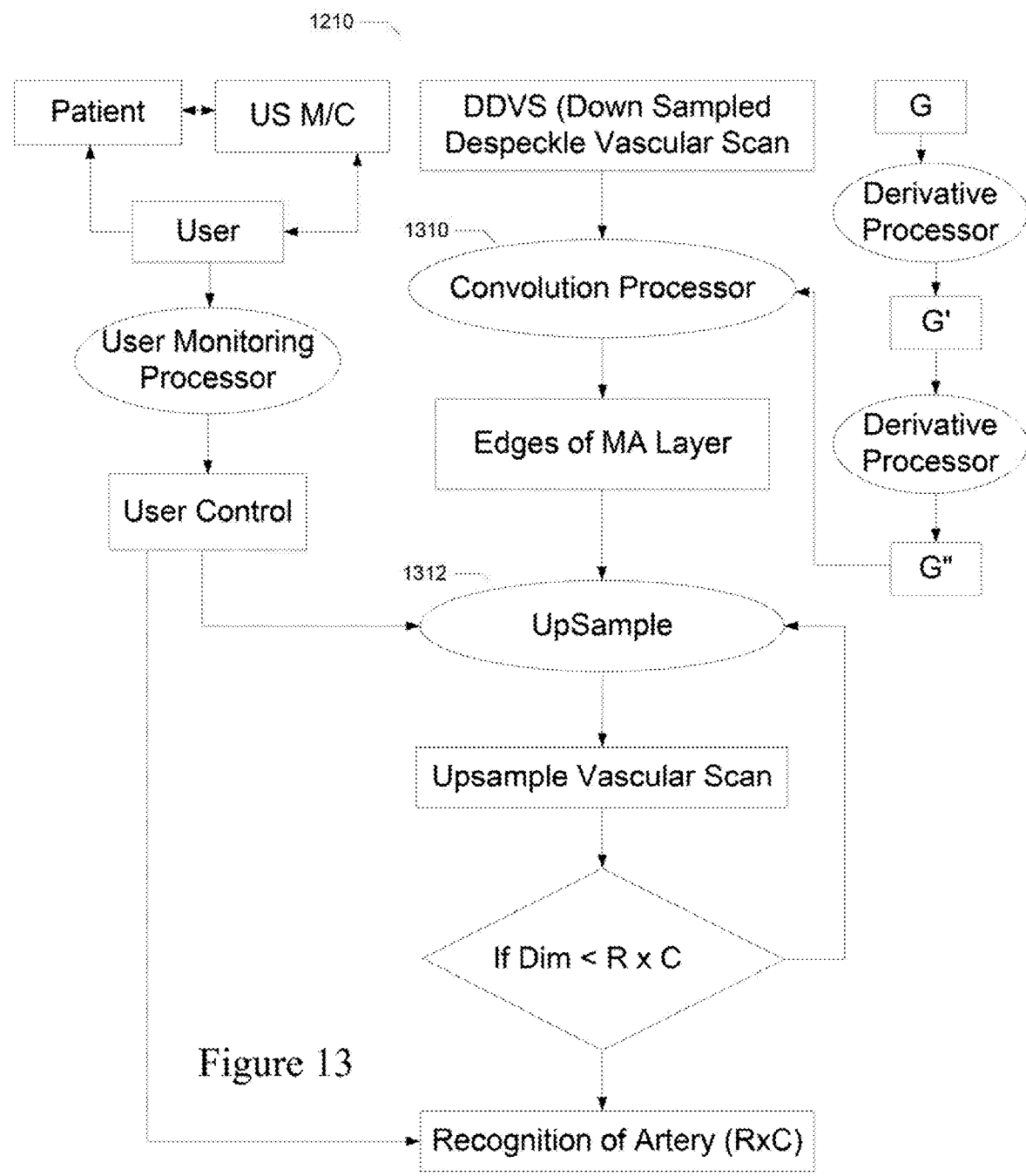
FIG. 13 shows the Artery Recognition Processor (a). This figure shows the artery recognition process of kind one, where the input image is the down sampled image of the cropped image. This figure also shows the edge detection of the MA border by convolution of higher order derivatives of Gaussian kernel with known mean and standard deviation. The figure also shows the up-sampling of the MA recognized border for visualization on to the high resolution cropped image.

FIG. 13 shows the Artery Recognition Processor which is the novelty of the patent as it does the automated recognition. It has two stages: (a) convolution and heuristic processor and (b) up-sample processor.

The convolution processor is used for convolution of the first order derivative G with the despeckled image. The scale parameter of the Gaussian derivative kernel was taken equal to 8 pixels, i.e. to the expected dimension of the IMT value. In fact, an average IMT value of say 1 mm corresponds to about 16 pixels in the original image scale and, consequently, to 8 pixels in the coarse or down sampled image. The convolution processor outcome will lead to the clear information for the near and far walls. This information will have two parallel bands corresponding to the far and near vessel walls. These bands will follow the curvature of the vessel walls. If the vessel wall is oriented downwards or upwards or has a bending nature, the bands will follow on both sides of the lumen. These bands have information which corresponds to the maximum intensity saturated to the maximum values of 2 power 8, the highest value. For an 8 bit image, this value will be 255.

The convolution process then allows the heuristics to estimate the Adventitia borders of the far wall or near wall. To automatically trace the profile of the far wall, this application uses heuristic search applied to the intensity profile of each column. Starting from the bottom of the image (i.e. from the pixel with the higher row index. The image convention uses (0,0) as top left hand corner of the image), we search for the first white region constituting of at least 6 pixels of width. The deepest point of this region (i.e. the pixel with the higher row index) marked the position of the far adventitia (ADF) layer on that column. The sequence the points resulting from the heuristic search for all the image columns constituted the overall automated far adventitia tracing ADF.

Figure 15:
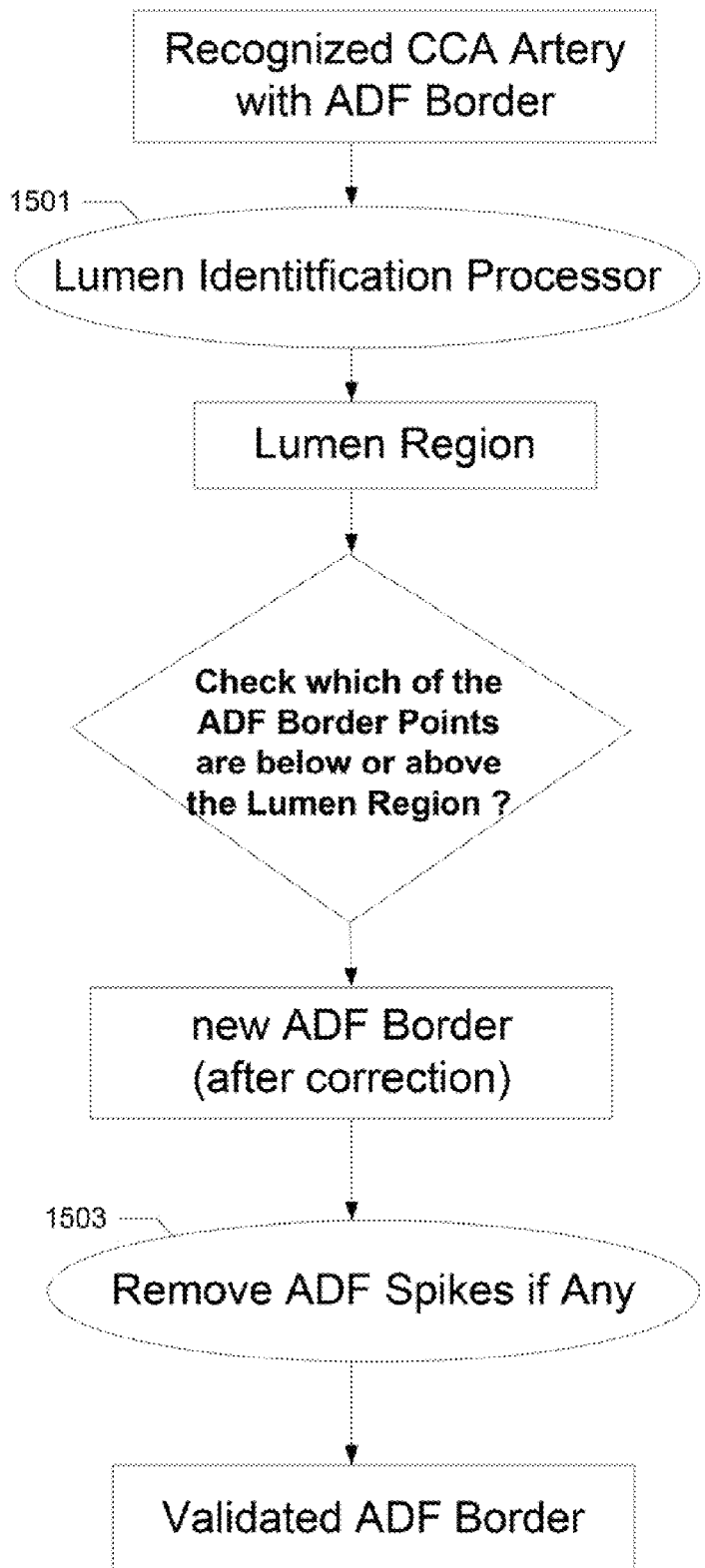
FIG. 15 shows the Artery Validation Processor. This figure shows the two main stages: (a) Lumen Identification Processor and (b) Spike Removal Processor.

FIG. 15 shows the Artery Validation Processor. Pilot studies showed that the traced ADF profile could be characterized by spikes and false points identification. This could be due to several reasons such as variations in intensities, gaps in the media walls, presence of jugular vein, shadow effects or combination of these. We have therefore introduced a validation protocol, which provides a check on the ADF profile ensuring that the location of CA is at correct place and the far adventitia segmentation edge is not very bumpy. This validation step refines the ADF profile and is done in two steps: (a) refinement using anatomic lumen and (b) spike removal.

Figure 16:
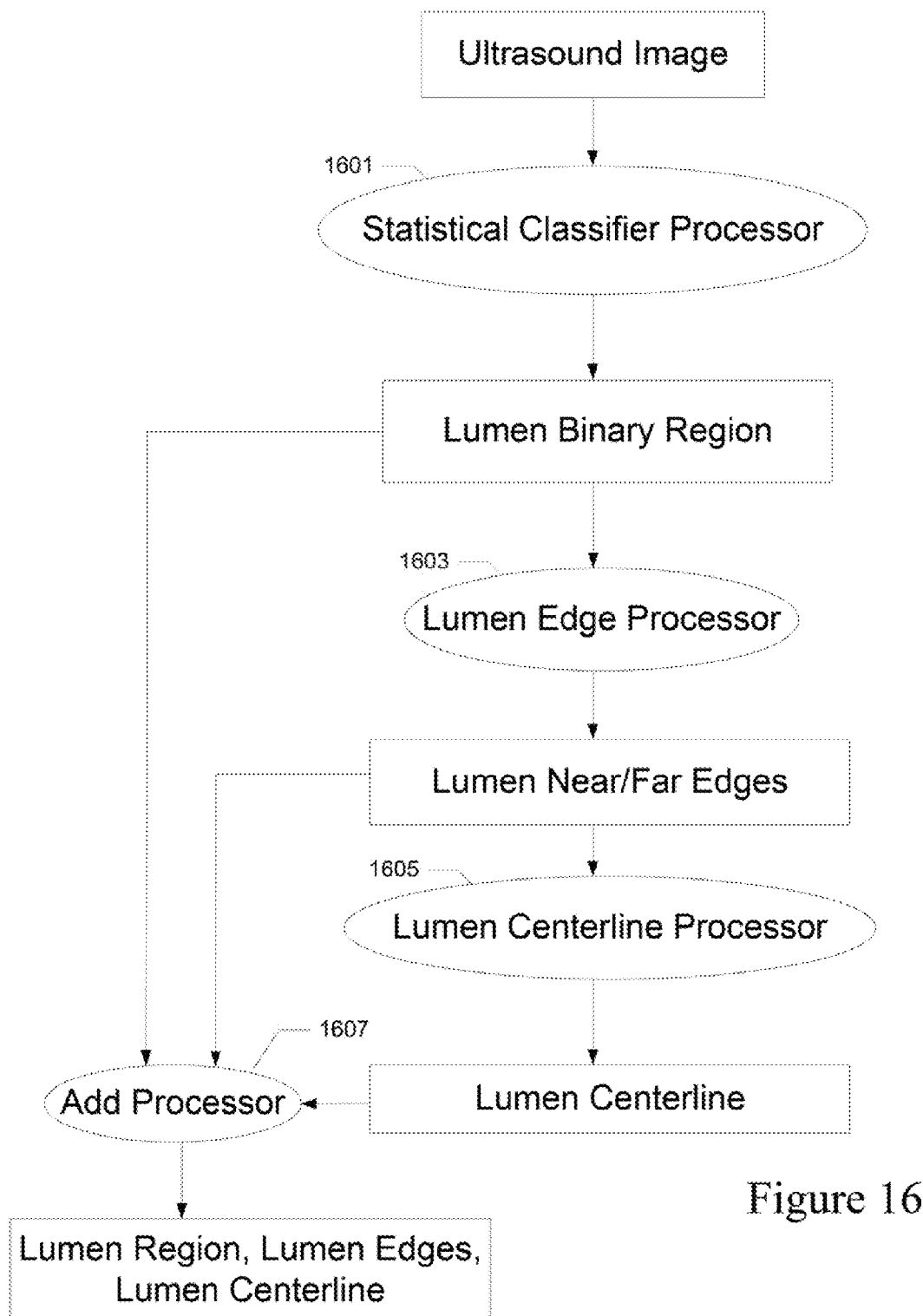
FIG. 16 shows the Lumen Identification Processor. It consists of three phases: (a) Lumen Classifier Processor; (b) Lumen Edge Processor; and (c) Lumen Centerline Processor.

FIG. 16 & FIG. 17 shows the Lumen Identification Processor Classifier Processor. This check has been introduced to avoid error conditions of ADF profile protruding into the lumen vessel or beyond. Thus, the refinement step first requires the identification of the lumen region automatically. We have modeled the lumen segmentation region as a classification process with two classes. Carotid characteristics can be thought of as a mixture model with varying intensity distributions. This is because (a) the pixels belonging to the vessel lumen are characterized by low mean intensity and low standard deviation; (b) pixels belonging to the adventitia layer of the carotid wall is characterized by high mean intensity and low standard deviation; and (c) all remaining pixels should have high mean intensity and high standard deviation. As a result of this distribution, we derived a bi-dimensional histogram (2DH) of the carotid image. For each pixel, we considered a 10×10 neighborhood of which we calculated the mean value and the standard deviation. The mean values and the standard deviations were normalized between 0 and 1 and were grouped into 50 classes each having an interval of 0.02. The number of classes equal to 50 and the corresponding class width of 0.02 had bee optimized in a previous study. The 2DH was then a joint representation of the mean value and standard deviation of each pixel neighborhood.

In previous studies, we showed that pixels belonging to the lumen of the artery are usually classified into the first few classes of this 2DH: expert sonographer manually traced the boundaries of the CCA lumen and observed the distribution of the lumen pixels on the 2DH. Overall results revealed that pixels of the lumen have a mean values classified in the first 4 classes and a standard deviation in the first 7 classes. We therefore consider a pixel as possibly belonging to the artery lumen if its neighborhood intensity is lower than 0.08 and if its neighborhood standard deviation is lower than 0.14. This shows how the local statistic is effective in detecting image pixels that can be considered as belonging to the CCA lumen. This segmented lumen region act as a check point for the ADF profile estimated before. We therefore utilize the lumen region as follows:

The ADF points along the CA are considered one by one. For each ADF point:

(a) Region of Interest Estimation ($ROI_L$): We consider the sequence of the 30 pixels above it (i.e., the 30 pixels located above the $AD_F$ point, towards the top of the image, and, therefore, with lower row indexes).

(b) Failure of $AD_F$ profile point: We test if the $ROI_L$ drawn around the $AD_F$ profile points cross the lumen region and have penetrated into the lumen region by at least 15 pixels or more (let's indicate this threshold value by $T_L$). If this does not happens, then the $AD_F$ profile point is considered to have failed the lumen test. Pilot experiments we conducted revealed that suitable values for $T_L$ are comprised between 12 and 20 pixels.

(c) Tagging of Profile Points: These failed $AD_F$ profile points must not belong to the $AD_F$ boundary. These $AD_F$ points which fail the lumen test are tagged as 0, while rest of the points are tagged as 1. $AD_F$ All the $AD_F$ points that tagged as 0 are deleted from the $AD_F$ list.

(d) The procedure is repeated for each $AD_F$ point along the CA artery.

Table 2 summarizes all the thresholds and parameters we used in AtheroEdge™. Tables 1 through 4 are provided below).

FIG. 17 C reports a sample of lumen test. FIG. 17 C (Part A, top left) shows the initial ADF guess in yellow color; FIG. 17 C (part B, top right) shows in red color those ADF points that failed the lumen test (crossed the lumen region). FIG. 17C (part C, bottom left) is the down sampled and despeckled image and FIG. 17 C (part D, bottom right) is the same image with the lumen pixels in white. The red dots are the ADF points that passed the lumen test (did not cross the lumen region). Note that even though, the lumen anatomic information, which acts as a reference, provides a good test for catching a series of wrongly computed ADF boundary, it might slip from sudden bumps which may be due to the changes in grayscale intensity due presence of unusual high intensity in lumen region or a calcium deposit in the near wall causing a shadow in far wall region. This sudden spike can then be easily detected ahead using the spike detection method.

Spike Detection and Removal.

Figure 17A:
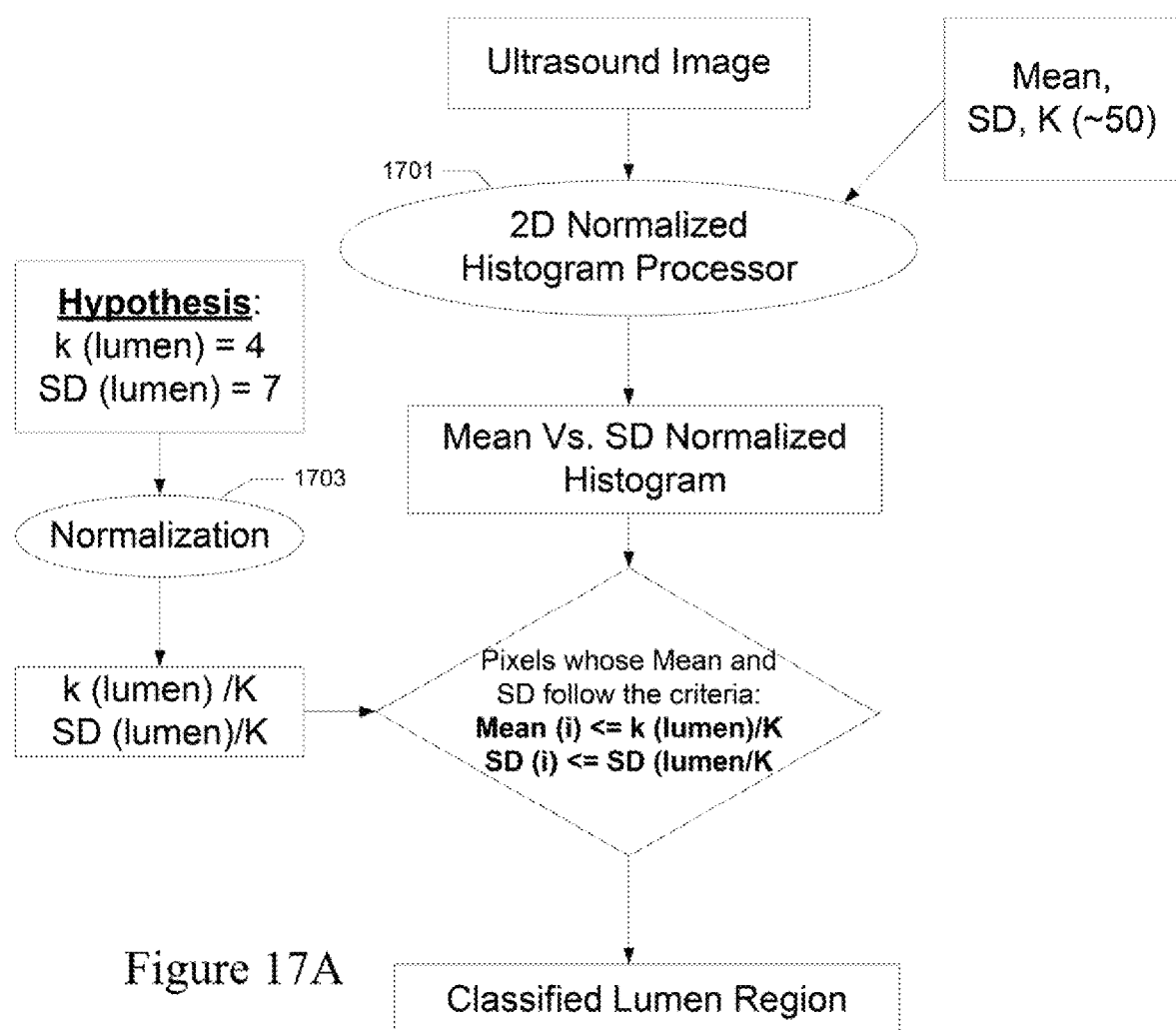
FIG. 17A shows the Classifier Processor. It consists of Histogram Processor and Decision Processor for evaluating the pixel classes.
Figure 17B:
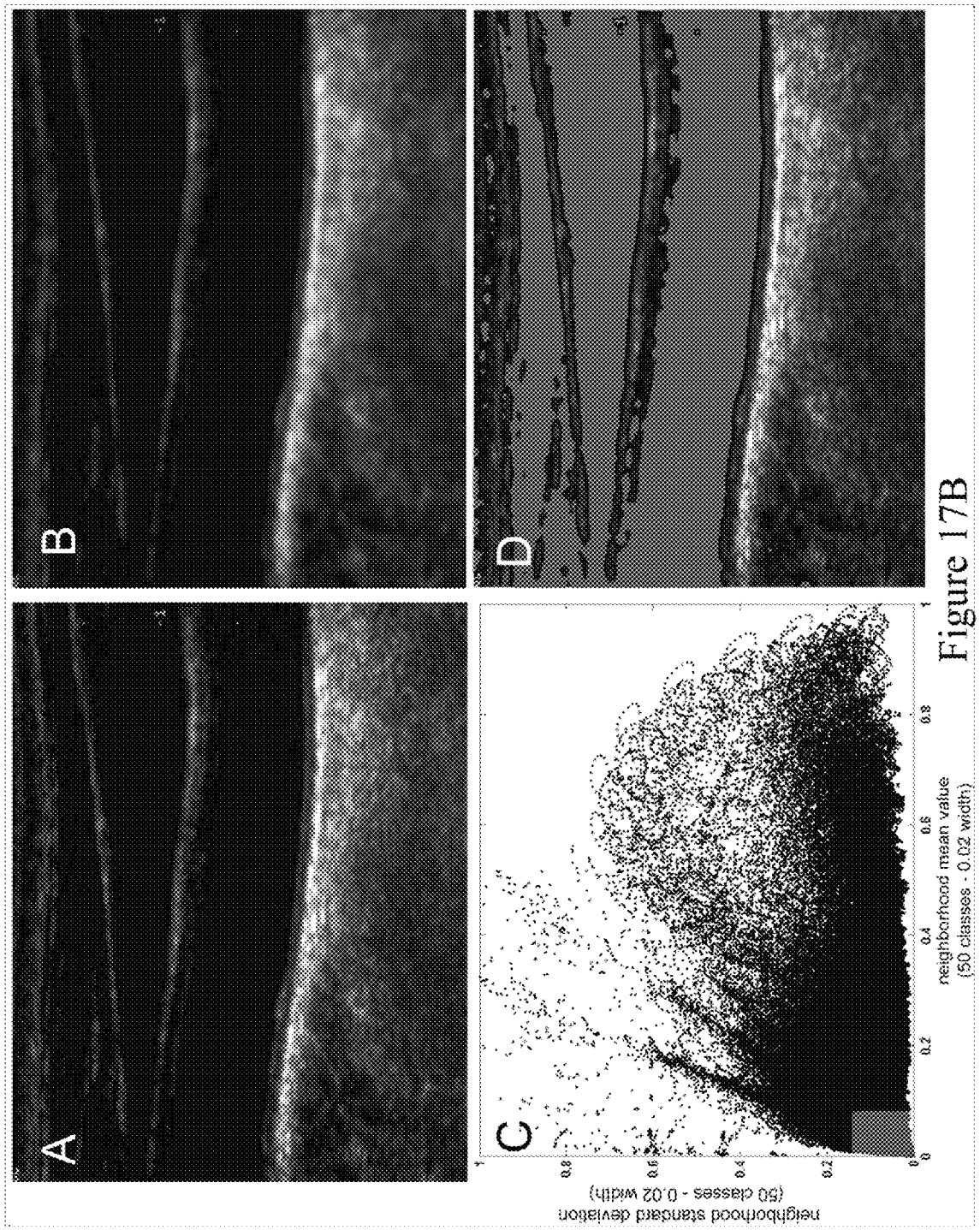
FIG. 17B shows A) Original B-Mode longitudinal image. B) Low-passed filtered image. C) 2DH showing in gray the histogram area where we hypothesize the lumen points should concentrate and in black all the other pixels. D) Lumen points (in gray) overlaid to the original B-Mode image of panel A.
Figure 17C:
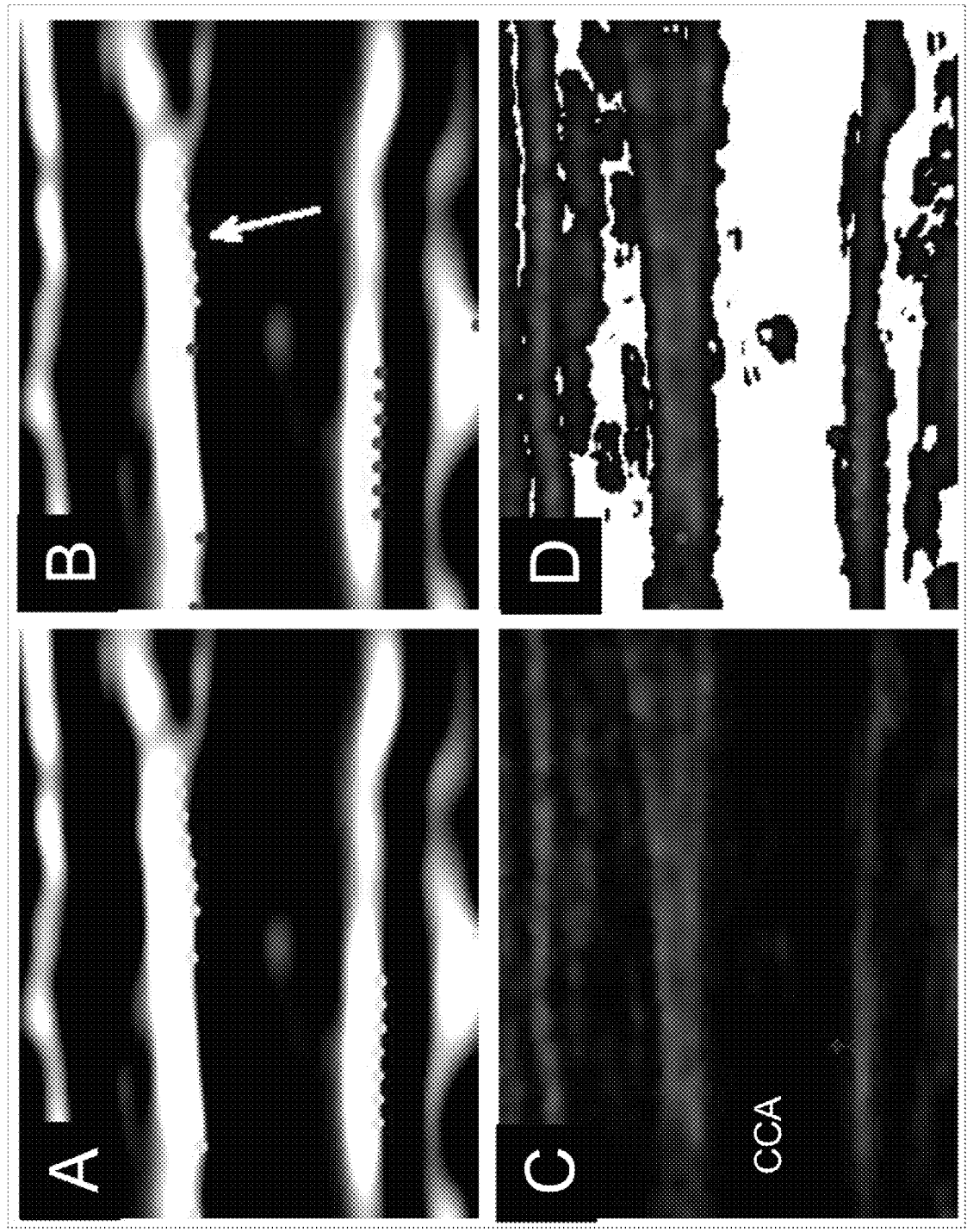
FIG. 17C shows A) Downsampled and filtered image (first-order Gaussian filter) with the initial $AD_F$ guess in yellow. B) The $AD_F$ points passing the lumen check are depicted in red. The white arrow indicates incorrect $AD_F$ points located on the near wall instead of the far wall that failed the lumen test and are deleted. C) Filtered image. D) $AD_F$ points (red dots) overlaid to the original image with lumen pixels in white.
Figure 17D:
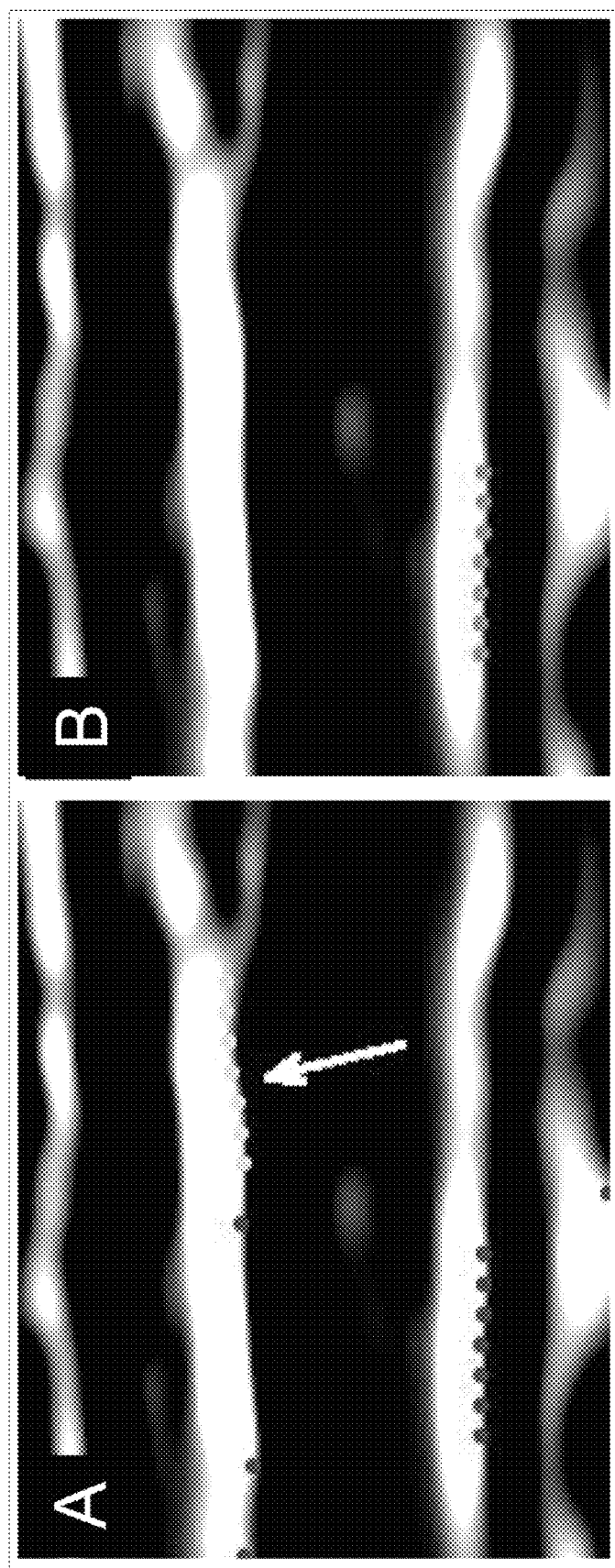
FIG. 17D shows A) Initial $AD_F$ guess (yellow dots) and $AD_F$ after lumen check (red dots). The white arrow indicates a series of dots located on the near wall, some of which pass the lumen test. These points originate spikes in the $AD_F$ profile. B) After the spike removal procedure, the $AD_F$ points are concentrated on the far wall (green dots).

We implemented an intelligent strategy for spike detection and removal. Basically, we compute the first order derivative of the ADF profile and check for values higher than TS=15 pixels. This value was chosen empirically by considering the image resolution. When working with images having approximate resolution of about 0.06 mm/pixel, an IMT value of 1 mm would be about 12-16 pixels. Therefore, a jump in the ADF profile of the same order of magnitude of the IMT value is clearly a spike and error condition. If the spike is at the very beginning of the image (first 10 columns) or at the end (last 10 columns), then the spiky point is simply deleted. Otherwise, all spikes are considered and either substituted by a neighborhood moving average or removed. FIG. 17D reports the spike removal procedure for the same image of FIG. 6. Final ADF points are represented by green dots.

The last stage of the Artery Recognition Processor is the up-sampling processor which allows the adventitia tracing ADF to be up-sampled back to the original scale of cropped image. The ADF profile was then up-sampled to the original scale and superimposed over the original cropped image for both visualization and determination of the region of interest for segmentation (or calibration) phase. At this stage, the CA far wall is automatically located in the image frame and automated segmentation is made possible.

Figure 14:
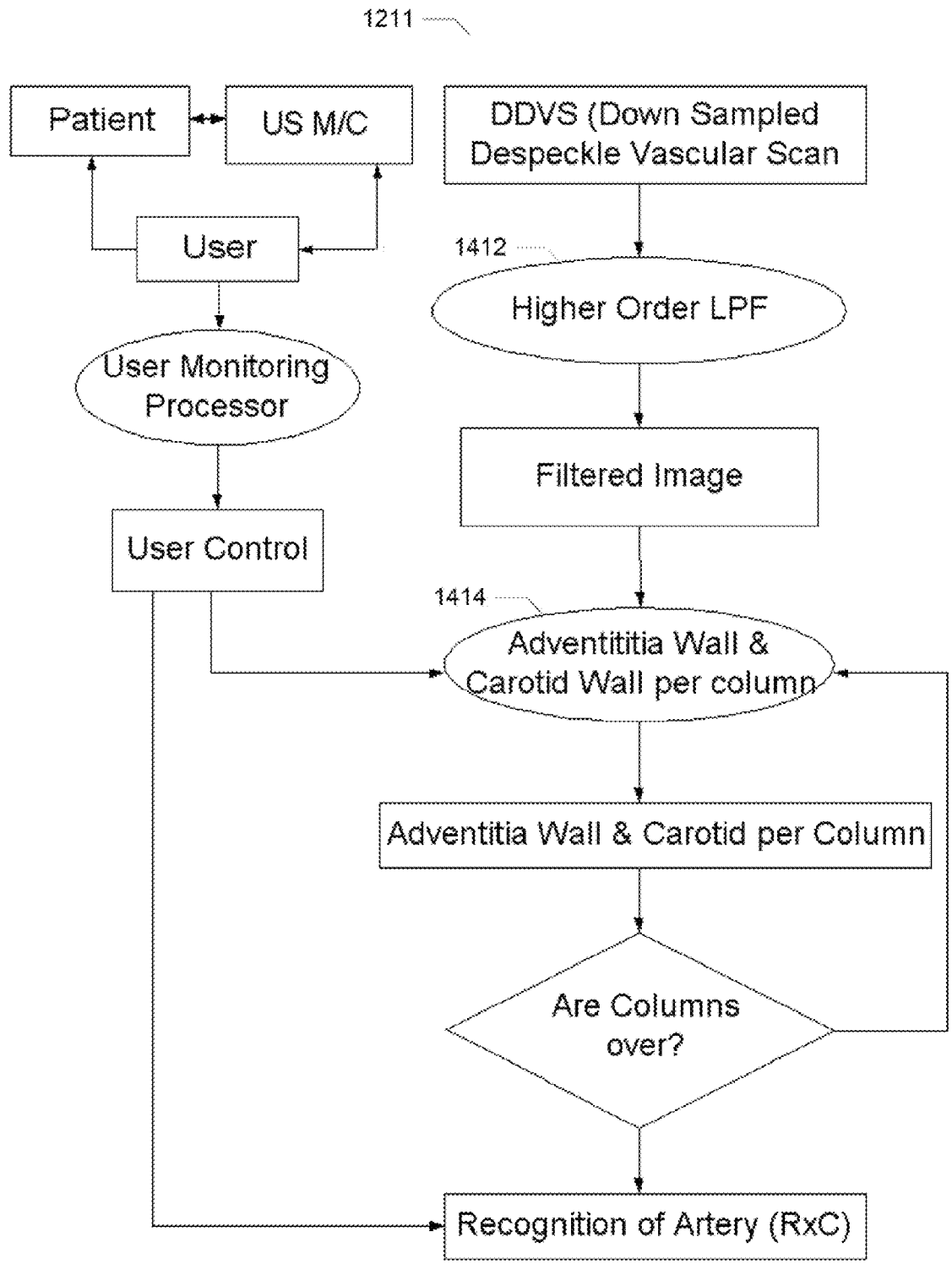
FIG. 14 shows the Artery Recognition Processor (b). It shows the calibration processor. This consists of three processors: (a) sub-ROI processor; (b) DoG processor and (c) convolution processor. The sub-ROI is generated by giving a pre-defined ROI given the recognized MA border. DoG process is computed by taking the difference of the Gaussian kernels. Convolution process is computed by taking the convolution of the Gaussian kernel with the DoG image.

This Artery Recognition Processor (stage-I) is the most innovative aspect of our methodology. It consists of a superior architecture based on fine to coarse sampling for vessel wall scale reduction, speckle noise removal, and higher-order Gaussian convolution, and automated validation embedded recognition of Adventitia. The ability of segmentation or calibration phase (stage-II) to be guided by the automated CA wall recognition is in itself a novel contribution. The first-order Gaussian kernel convolution allowed for an optimal detection of the CA walls. This kernel has unitary energy. When such kernel is located in proximity of a neat gray level change, it enhances the transition. Consequently, the most echoic image interfaces are enhanced to white in the filtered image. For this reason, the Artery Recognition Processor allows for detecting the adventitia layer. Those skilled in the art can make another combination of Artery Recognition Processor and a calibration system; for example, FIG. 14 shows another Artery Recognition Processor based on the combination of LPF and Peak Detection system. This can also be connected to the calibration system (stage-II). This Artery Recognition Processor several advantages to it:

(1) Robustness and Accurate Wall Capture: it is very robust because the higher order derivative kernels are very good in capturing the vessel walls (see, A Review on MR Vascular Image Processing Algorithms: Acquisition and Pre-filtering: Part 1, Suri et al., IEEE TRANSACTIONS ON INFORMATION TECHNOLOGY IN BIOMEDICINE, VOL. 6, NO. 4, pp. 324-337, December 2002; and A Review on MR Vascular Image Processing:Skeleton Versus Nonskeleton Approaches: Part II, Suri et al., *IEEE TRANSACTIONS ON INFORMATION TECHNOLOGY IN BIOMEDICINE*, VOL. 6, NO. 4, DECEMBER 2002).

(2) Easter than the conventional processing: Since the recognition is strategized at coarse level down sampled twice from its original size of the image, it is therefore processing $\frac{1}{4}^{th}$ the number of pixels for automated recognition of the media layer. This improves the speed of the system.

(3) Independent of Orientation of the vascular scan: Another major advantage to the system is that these Gaussian kernels are independent of the orientation of the blood vessels in the image. Since the ultrasound vascular scans do not always have the vessel orientation horizontal with respect bottom edge of the image, manual methods can pose a further challenge towards the region of interest estimation.

(4) Guiding Method for the Calibration System: Since the recognition is followed by the calibration process, the calibration system becomes very robust since the calibration processing is done in the region of interest determined by the automated recognition system. Thus the calibration system adds the value determined by the automated recognition system for vascular ultrasound such as IMT measurement for carotid, femoral, aortic and brachial. Such a combination where the calibration system is guided by the automated recognition system helps in mass processing of huge database processing.

(5) Running the Mass IMT system for Clinical Analysis: Since the recognition is automated followed by the calibration system, the largest value such a system would deliver will be in its real time use for analysis of IMT measurement on a large databases. Running clinical databases on still images would be even more beneficial because such a system would be completely automated in terms of recognition and IMT measurement.

(6) Applications: Since the ultrasound probes use almost the same frequency of operation for scanning the vascular arteries such as carotid, femoral, brachial and aortic, it is thus possible to use such a system for these blood vessels.

Figure 18:
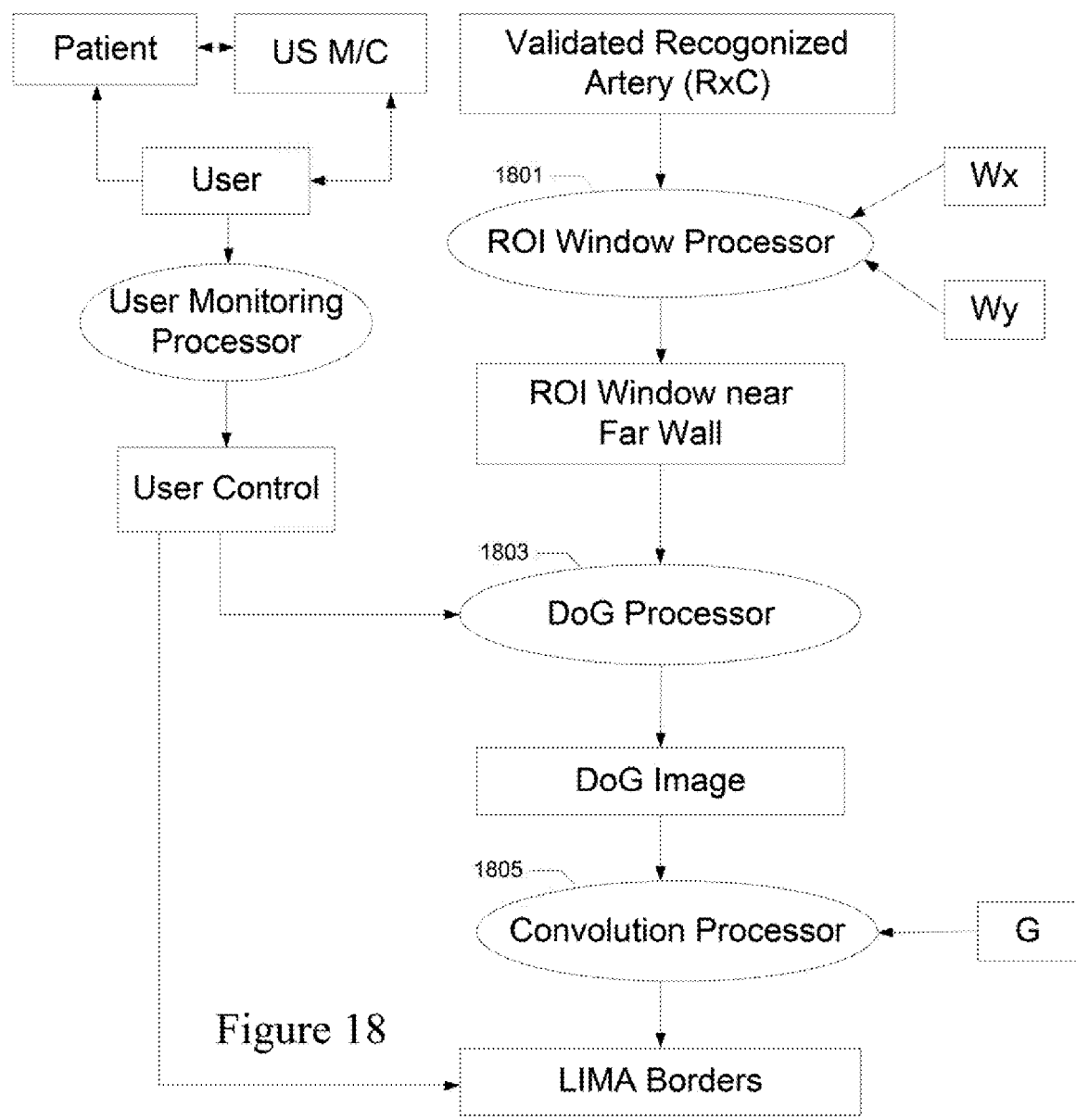
FIG. 18 shows the Calibration Processor showing the DoG Filtering.
Figure 19:
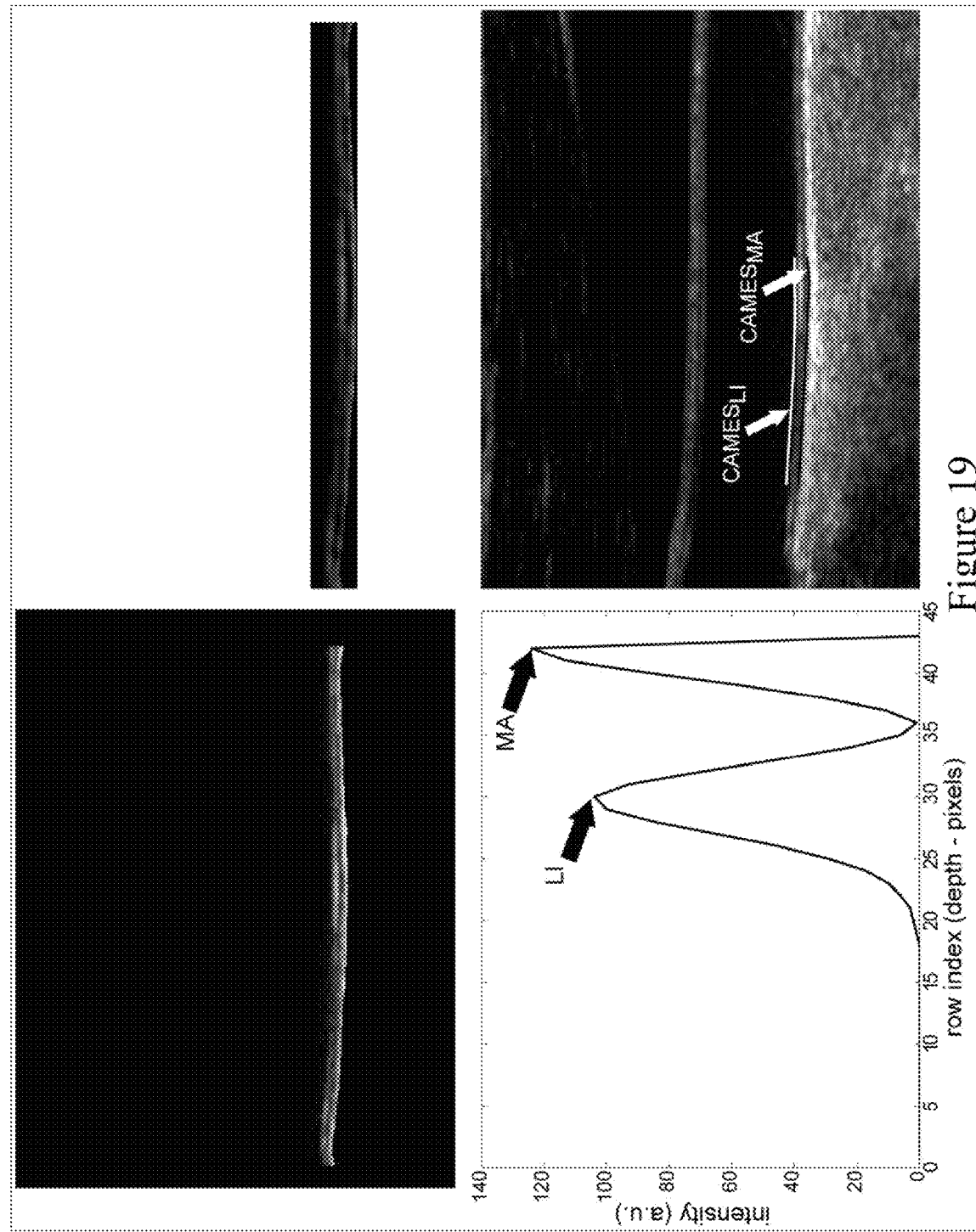
FIG. 19 shows the Peak detector for stage II using the multi-resolution framework.
Figure 20:
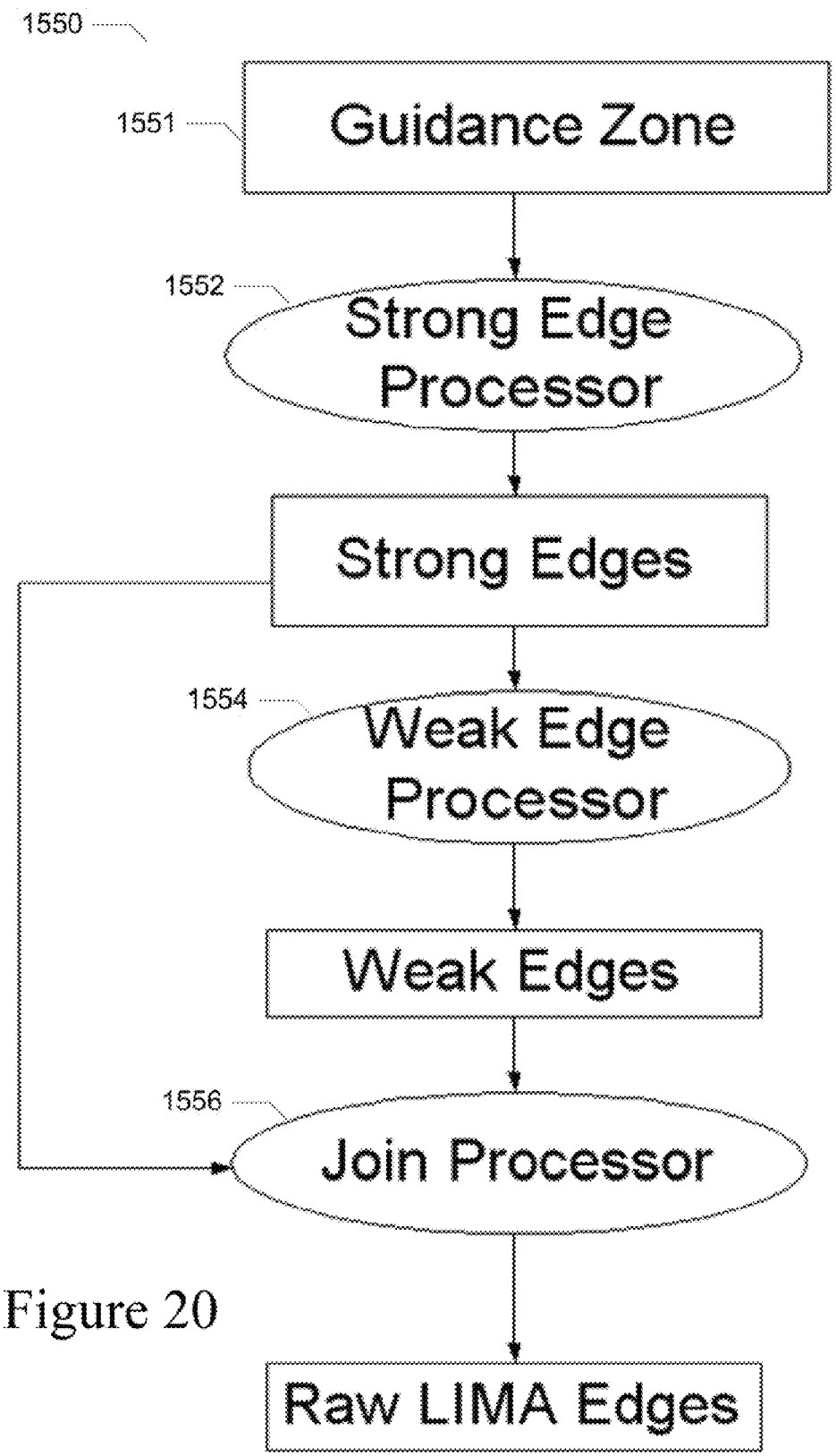
FIG. 20 shows the Calibration processor using edge flow (type II for stage II).

FIGS. 18, 19 and 20 shows the Calibration Processor. The output of the multi-resolution strategy provides the automated recognition of the distal wall in the carotid B-mode ultrasound images. Stage-II is focused narrowly in the region of interest, where the objective is to estimate the LI/MA borders accurately. Here we model a filter in the guidance zone, such that the operation allows for acting as a high pass filter enhancing the intensity edges. For ultrasound images, such a filter can be thought as a Multi-resolution First Order Absolute Moment (MRFOAM) amplified by the Gaussian Kernel with known scale factor. These filtered edges are then heuristically captured to build the LI and MA segmentation borders in the far wall of the carotid artery in the image frame. This automated segmentation strategy is sub-divided into three steps as follows:

Step 1: Creation of the Guidance Zone.

We built a region-of-interest (ROI) or guidance zone (GZ) around the automatically traced far adventitia ADF profile, so called the domain region in which pixel processing was done to estimate LI and MA borders. Note that the GZ must have a region whose envelope is at least same length as the width of the ADF curve along the carotid artery. From the database, we observed that the average internal diameter of the human common carotid artery is 6 mm, which corresponds to be about 100 pixels. Since the total wall thickness for the near and far wall when combined to be around 30 pixels, which comes to one-third of the lumen diameter, we therefore decided to keep the envelope's height of the GZ to be around ⅓rd the lumen diameter, which was around 30 pixels. Thus the guidance zone (GZ) had a width same as ADF profile and height of 30 pixels. This constituted the ROI whose bottom limit was the ADF curve, while the upper limit was shifted upwards (upper edge of the image) by 30 pixels w.r.t ADF curve.

Step 2: Edge Enhancement Gradient of Gaussian (GoG) Filtering: MRFOAM. Operator.

We used the Multi-resolution First Order Absolute Moment (MRFOAM) operator for final segmentation of LI and MA borders in the automatically designed guidance zone obtained from the multi-resolution approach. The FOAM operator is a regularized edge-based operator, was first introduced by Demi et al. [M Demi, M. Paterni, and A. Banassi, "*The first absolute central moment in low-level image processing,*" Computer Vision and Image Understanding, vol. 80, no. 1, pp. 57-87, October, 2000] and then applied to accurate semi-automated IMT measurement in ultrasound images by Faita et al. [F. Faita, V. Gemignani, E. Bianchini, C. Giannarelli, L. Ghiadoni, and M. Demi, "*Real-time measurement system for evaluation of the carotid intima-media thickness with a robust edge operator,*" J Ultrasound Med, vol. 27, no. 9, pp. 1353-61, September, 2008]. Considering an image l(x,y) and two circular domains having radiuses equal to $\theta_1$ and $\theta_2$, respectively, the FOAM edge e(x,y) operator is mathematically defined as:

$$e(x, y) = \int\int_{\theta_2} |I_1(x, y) - I(x-k, y-l)| \cdot G(k, l, \sigma_3) dk dl \quad (6)$$

where $$I_1(x, y) = \int\int_{\theta_1} I(x-k, y-l) \cdot G(x, y, \sigma_l) dk dl$$

and is computed by low-pass filtering the input image by a Gaussian kernel with standard deviations equal to $\sigma_l$ and domain region equal to $\theta_1$. The FOAM operator represents the spatial distribution of the variability of the intensity levels of the points in the domain $\theta_2$ with respect to the average of the domain $\theta_1$, with a regularization Gaussian kernel with standard deviation equal to $\sigma_3$. Therefore, in homogeneous regions (i.e. in regions without intensity changes and that are of the same gray level), the MRFOAM edge value is close to zero. When computed in proximity of an intensity gradient, the MRFOAM edge value rises to a maximum. Gemignani et al. optimized the values of $\theta_1$ and $\theta_2$ for ultrasound vascular images and suggested to link the Gaussian Kernel sizes to the image resolution [24]. Also, they suggested using a value of $\sigma$ equal to ⅓$^{rd}$ of the kernel size. This ensured optimized representation of the intensity discontinuities (i.e. in this specific case, of the interfaces between the carotid layers).

Recently, Faita et al. showed that better robustness to noise can be achieved by adopting a third Gaussian Kernel function and proposed adopting the following definition:

$$e(x,y) = \iint |I_1(x,y) - I_2(x-k, y-l)| \cdot G(k,l,\sigma_3) dk dl \quad (7)$$

where $I_1(x,y) = I(x,y) \otimes G(x,y,\sigma_1)$ and $I_2(x,y) = I(x,y) \otimes G(x,y,\sigma_2)$ are computed by low-pass filtering the input image by a Gaussian kernel with standard deviations equal to $\sigma_1$ and $\sigma_2$, respectively. The use of two different apertures values $\sigma_1$ and $\sigma_2$ implements a filter that is similar to the Gradient-of-Gaussians (GoG) filter, which is a high-pass filter, enhancing the intensity edges. The regularization term $G(x,y,\sigma_3)$ is Gaussian filter with standard deviation equal to $\sigma_3$. We linked the Gaussian Kernel sizes and $\sigma$ values to the image calibration factor (the best calibration factor was CF=0.06 mm/pixel, as reported by Table 1), and chose the value of PC=0.3 mm for the pixel conversion (PC). Hence, we used the kernel size $\theta_1 = \theta_3 = PC/CF$, where CF is the conversion factor. This yields, $\theta_1 = \theta_3 = 0.3/0.06 = 5$ pixels. As suggested by Faita et al. [4], we took $\theta_2 = 2\theta_1 = 10$ pixels. The Gaussian Kernel parameters were then taken equal to:

$$\sigma_1 = \sigma_3 = [\theta_1/3] = 2 \text{ pixels}$$

$$\sigma_2 = [\theta_2/3] = 3 \text{ pixels} \quad (8)$$

Table 2 summarizes the parameters we used in our AtheroEdge™ technique. The value of 0.3 mm value was similar to that adopted by Faita et al., who used a value of 0.28 mm. We observed that higher values originated larger Gaussian Kernels, which decreased the accuracy of the LI/MA representation and, therefore, decreased the MRFOAM localization performance. Conversely, values lower than 0.3 mm originated very small Gaussian Kernels, which did not ensure sufficient noise robustness.

FIG. 18 shows the Calibration Processor showing the DoG Filtering.

FIG. 19 shows the Peak detector for stage II using the multi-resolution framework. This uses the Heuristic Approach for LI/MA Border Detection. The LI and MA edge interfaces were then searched by relying on heuristic search. The LI and MA transitions produce two high-intensity peaks on the FOAM column profile, which can be automatically marked. We model the MA and LI peak selection locations as the $90^{th}$ percentile of the intensity distribution along that column. Thus, starting from the position of the far adventitia (marked by ADF), the first intensity absolute maximum that reflects the $90^{th}$ percentile of the intensity distribution for that column is marked as the MA interface location. We continue the search ahead in the direction of the decreasing row index (i.e., towards the top or proximal wall of the image) and again the location is searched which reflects $90^{th}$ percentile of the intensity distribution, marked as the LI interface. This procedure is repeated column-by-column along the CA artery until all the points along the ADF curve are examined. If one of the two maxima's is not found, that column is discarded. A subsequent outlier removal step cleans disconnected columns and regularizes the profiles, ensuring the constraint that a maximal distance between LI and MA is lower than 2 mm. This regularization step ensures an optimal representation of the LI/MA profiles in healthy arteries or in arteries with increased IMT, but it is not suited to plaque analysis.

FIG. 20 shows the Calibration process of type II (using Edge Flow Calibration Processor). This shows the domain based calibration process or segmentation processor. The system is divided into three components: (a) Guidance Zone Peocessor; (b) DoG Filtering Processor; (c) Heuristic Processor. Since the Artery Recognition Processor has identified the adventitia tracing ADF, the calibration needs to be applied in the zone which was initially guided by the Artery Recognition Processor. Since the calibration stage is merely a combination of finding the edges of the LI and MA borders, the importance of guidance zone is very crucial. The Guidance Zone is the key to avoid the false peaks estimation in the calibration phase.

The Guidance Zone is built around the adventitia tracing ADF. The Guidance Zone is a region-of-interest (ROI) around the automatically traced ADF profile, so called the domain region in which segmentation will run. The ROI is designed such that it has the same width as of the ADF curve. This will allow the creation of the largest possible ROI, according to the detected length of the adventitia layer. The height has to be equal to 30 pixels (1.8 mm for images with 16.67 pixels/mm of density, and 1.875 mm for images with 16 pixels/mm of density). For each point of the ADF profile we considered as upper limit of the ROI the pixel with a row index of 30 pixels lower, towards the upper edge of the cropped image. Substantially, the bottom limit of the ROI was the ADF curve while the upper limit was ADF shifted by 30 pixels.

Edge Flow Magnitude and Edge Flow Direction: We use the method developed by W. Y. Ma and B. S. Manjunath (citation: Ma, W. Y. and B. S. Manjunath. *Edge Flow: A Framework of Boundary Detection and Image Segmentation* in *Computer Society Conference on Computer Vision and Pattern Recognition*. 1997. San Juan).

that facilitates the integration of different image attributes into a single framework for boundary detection and is based on the construction of an edge flow vector defined as:

$$F(s,\theta)=F[E(s,\theta),P(s,\theta),P(s,\theta+\pi)] \quad (2)$$

where:
$E(s,\theta)$ is the edge energy at location s along the orientation $\theta$;
$P(s,\theta)$ represents the probability of finding the image boundary if the corresponding edge flow "flows" in the direction $\theta$;
$P(s,\theta+\pi)$ represents the probability of finding the image boundary if the edge flow "flows" backwards, i.e., in the direction $\theta+\pi$.

The final single edge flow vector can be thought of as the combination of edge flows obtained from different types of image attributes. The image attributes that we considered are intensity and texture. In order to calculate the edge energy and the probabilities of forward and backward edge flow direction, a few definitions must first be clarified, specifically the first derivative of Gaussian (GD) and the difference of offset Gaussian (DOOG).

Considering the Gaussian kernel $G_\sigma(x,y)$, where $\sigma$ represents the standard deviation, the first derivative of the Gaussian along the x-axis is given by $$GD_\sigma(x,y) = -\left(\frac{x}{\sigma^2}\right)G_\sigma(x,y) \quad (3)$$

and the difference of offset Gaussian (DOOG) along the x-axis is defined as:

$$DOOG_\sigma(x,y)=G_\sigma(x,y)-G_\sigma(x+d,y) \quad (4)$$

where d is the offset between centers of two Gaussian kernels and is chosen proportional to C. This parameter is significant in the calculation of the probabilities of forward and backward edge flow, as it is used to estimate the probability of finding the nearest boundary in each of these directions. By rotating these two functions, we can generate a family of previous functions along different orientations $\theta$ and they can be denoted as $G_{\sigma,\theta}(x,y)$ and $DOOG_{\sigma,\theta}(x,y)$, respectively:

$$GD_{\sigma,\theta}(x,y)=GD_\sigma(x',y') \quad (5)$$

$$DOOG_{\sigma,\theta}(x,y)=DOOG_\sigma(x',y') \quad (6)$$

where: x'=x cos $\theta$+y sin $\theta$, and y'=−x sin $\theta$+y cos $\theta$

Intensity Edge Flow: Considering the original image I(x,y) at a certain scale $\sigma$, $I_\sigma(x,y)$ is obtained by smoothing the original image with a Gaussian kernel $G_\sigma(x,y)$. The edge flow energy $E(s,\theta)$ at scale $\sigma$, defined to be the magnitude of the gradient of the smoothed image $I_\sigma(x,y)$ along the orientation $\theta$, can be computed as $$E(s,\theta)=|I(x,y)*GD_{\sigma,\theta}| \quad (7)$$

where s is the location (x,y). This energy indicates the strength of the intensity changes. The scale parameter is very important in that it controls both the edge energy computation and the local flow direction estimation so that only edges larger than the specified scale are detected.

To compute $P(s,\theta)$, two possible flow directions ($\theta$ and $\theta+\pi$) are considered for each of the edge energies along the orientation $\theta$ at location s. The prediction error toward the surrounding neighbors in these two directions can be computed as:

$$\text{Error}(s,\theta)=|I_\sigma(x+d\cos\theta,y+d\sin\theta)-I_\sigma(x,y)|=|I(x,y)*DOOG_{\sigma,\theta}(x,y)| \quad (8)$$

where d is the distance of the prediction and it should be proportional to the scale at which the image is being analyzed. The probabilities of edge flow direction are then assigned in proportion to their corresponding prediction errors, due to the fact that a large prediction error in a certain direction implies a higher probability of locating a boundary in that direction:

$$P(s, \theta) = \frac{\text{Error}(s, \theta)}{\text{Error}(s, \theta) + \text{Error}(s, \theta + \pi)} \quad (9)$$

Texture Edge Flow: Texture features are extracted from the image based on Gabor decomposition. This is done basically by decomposing the image into multiple oriented Spatial frequency channels, and then the channel envelopes (amplitude and phase) and used to form the feature maps.

Given the scale σ, two center frequencies of the Gabor filters (the lowest and the highest) are defined and based on the range of these center frequencies, an appropriate number of Gabor filters $g_i(x,y)$ is generated. The complex Gabor filtered images are defined as:

$$O_i(x,y) = I * g_i(x,y) = m_i(x,y) \exp[\Phi_i(x,y)] \quad (10)$$

where $1 \leq i \leq N$, N is the total number of filters and i is the sub band, $m_i(x,y)$ is the magnitude, and $\Phi_i(x,y)$ is the phase. A texture feature vector $\Psi(x,y)$ can then be formed by taking the amplitude of the filtered output across different filters at the same location (x,y):

$$\Psi(x,y) = [m_1(x,y), m_2(x,y), \ldots, m_N(x,y)] \quad (11)$$

The change in local texture information can be found using the texture features, thus defining the texture edge energy:

$$E(s, \theta) = \sum_{1 \leq i \leq N} |m_i(x, y) * GD_{\sigma,\theta}(x, y)| \cdot w_i \quad (12)$$

where $$w_i = \frac{1}{\|\alpha_i\|}$$

and $\nu\alpha_i\nu$ is the total energy of the sub band i.

The direction of the texture edge flow can be estimated similarly to the intensity edge flow, using the prediction error:

$$\text{Error}(s, \theta) = \sum_{1 \leq i \leq N} |m_i(x, y) * DOOG_{\sigma,\theta}(x, y)| \cdot w_i \quad (13)$$

and the probabilities $P(s,\theta)$ of the flow direction can be estimated using the same method as was used for the intensity edge flow.

Combining Edge Flow from Intensity and Texture: For general-purpose boundary detection, the edge flows obtained from the two different types of image attributes can be combined:

$$E(s, \theta) = \sum_{a \in A} E_a(s, \theta) \cdot w(a), \quad \sum_{a \in A} w(a) = 1 \quad (14)$$

$$P(s, \theta) = \sum_{a \in A} P_a(s, \theta) \cdot w(a) \quad (15)$$

where $E_a(s,\theta)$ and $P_a(s,\theta)$ represent the energy and probability of the edge flow computed from the image attributes a (in this case, it is intensity and texture). w(a) is the weighting coefficient among various types of image attributes. To identify the best direction for searching for the nearest boundary, we are supposed to have edge flows $\{F(s,\theta)|_{0 \leq \theta \leq \pi}\}$ and identify a continuous range of flow directions which maximizes the sum of probabilities in that half plane:

$$\Theta(s) = \arg\max_{\theta} \left\{ \sum_{\theta \leq \theta' \leq \theta + \pi} P(s, \theta') \right\} \quad (16)$$

The vector sum of the edge flows with their directions in the identified range is what defines the final resulting edge flow and is given by:

$$\vec{F}(s) = \sum_{\Theta(s) \leq \theta \leq \Theta(s) + \pi} E(s, \theta) \cdot \exp(j\theta) \quad (17)$$

where $\vec{F}(s)$ is a complex number whose magnitude represents the resulting edge energy and whose angle represents the flow direction.

Flow Propagation and Boundary Detection

Once the edge flow $\vec{F}(s)$ of an image is computed, boundary detection can be performed by iteratively propagating the edge flow and identifying the locations where two opposite direction of flows encounter each other. The local edge flow is then transmitted to its neighbor in the direction of flow if the neighbor also has a similar flow direction. The steps which describe this iterative process are as follows:

STEP 1: Set n=0 and $\vec{F}_0(s) = \vec{F}(s)$

STEP 2: Set the initial edge flow $\vec{F}_{n+1}(s)$ at time n+1 to zero

STEP 3: At each image location s=(x,y), identify the neighbour s'=(x',y') which is in the direction of edge flow $\vec{F}_n(s)$ STEP 4: Propagate the edge flow if $\vec{F}_n(s') \cdot \vec{F}(s) > 0$ $$\vec{F}_{n+1}(s') = \vec{F}_{n+1}(s') + \vec{F}_n(s):$$

otherwise, $$\vec{F}_{n+1}(s) = \vec{F}_{n+1}(s) + \vec{F}_n(s)$$

STEP 5: If nothing has been changed, stop the iteration. Otherwise, set n=n+1 and go to step 2.

The image boundaries can then be detected once the edge flow propagation reaches a stable set by identifying the locations which have non-zero edge flow coming from two opposing directions. For all of the images, we considered 8 different orientations, starting from 0° and going to 315° with equal degree intervals in between. FIG. 20 shows the main system for stage II using edge flow method.

Once the image boundaries are detected, the final image is generated by performing region closing on it to limit the number of disjoint boundaries by searching for the nearest boundary element, which is within the specified search neighborhood at the unconnected ends of the contour. If a boundary element is found, a smooth boundary segment is generated to connect the open contour to another boundary element. The neighborhood search size is taken to be proportional to the length of the contour itself.

This approach of edge detection has some very salient features, including the fact that it uses a predictive coding model for identifying and integrating the different types of image boundaries, the boundary detection is based on flow field propagation and it has very few "free" parameters that control the segmentation. Because of this, very little parameter tuning or selection is needed and the sole parameter that controls the segmentation is the preferred image scale.

The edge flow algorithm can over-segments in many different points, due partly to the fact that the image can be cropped to contain the entire Guidance Zone Mask and therefore may contain sections of the image that can be found below the ADF profile. Also, while part of the MA and LI edge estimation may be done using the edge flow algorithm, the segmentation cannot yet be considered complete as there are still some missing MA and LI edges and the edges found must be classified as either belonging to the MA profile or the LI profile. This refinement and classification process is done using a strong dependency on the edges found by the edge flow algorithm and via labeling and connectivity, which will be explained in further detail in the next two sections.

FIG. 20 shows the MA weak/missing edge estimation using MA strong edge dependency via labeling and connectivity and complete MA estimation: In this step all the edge objects in the output image that are not included in the Guidance Zone are eliminated, thus discarding many of the over-segmented edge objects found below the ADF profile. An edge object is defined as a connected component in the binary image.

Small Edge Objects: Secondly, since there can still be small unwanted edge objects around the interested area, small edge objects are defined as those which have an area ratio below a certain limit $\phi$ and are subsequently removed from the image. The area ratio is defined by the following equation:

$$AreaRatio = \frac{Area_{EdgeObject}}{Area_{AllEdgeObjects}} \leq \phi \Rightarrow SmallEdgeObject \quad (18)$$

MA Estimation: Our experimental data showed that, when $\phi=0.1$ we are successfully able to discard the small edge objects. The MA segment is then first initialized as being the edge object with the highest pixel row index (i.e., the lowest edge object in the image) and its unconnected end points are found as the right top and left top pixels of the edge object (RTMA and LTMA, respectively). The remaining edge objects are then sorted by their mean pixel row index value so as to examine the edge objects starting from those which are lowest in the image and working upwards. The edge objects are then classified by following these steps:

1. Find the unconnected end points of the i-th edge object as the right top and left top pixels of the examined edge object ($RT_i$ and $LT_i$, respectively).
2. Determine the correct unconnected end point pair (either $LT_{MA}$ and $RT_i$ or $LT_i$ and $RT_{MA}$) as the pair which yields a lesser column difference in absolute value:

$$|LT_{x_{MA_i}} - RT_{x_{i_{MA}}}| \quad (19)$$

3. Calculate the respective row distance in absolute value ($|LT_y-RT_y|$) and column distance ($LT_x-RT_x$) between the correct unconnected end point pair found and determine that the examined edge object can be classified as being part of the MA segment if the following two conditions are met:

$$|LT_y - RT_y| \leq \phi \quad (20)$$

$$LT_x - RT_x > 0 \quad (21)$$

where $\phi$ is the maximum row distance acceptable, which we took to be equal to 15. The condition on the column distance is needed to ensure that the edge object considered does not overlap the already existing MA segment, while the condition on the row distance is necessary so as to avoid including edges that are too far above the existing MA segment.

4. Find new unconnected end points of the MA segment.
5. Repeat steps 1-4 until all edge objects have been examined.

Once all of the edge objects have been examined, those which are classified as being part of the MA segment are then connected together and regulated using a B-spline to produce the final MA profile.

FIG. 20 LI weak/missing edge estimation using LI strong edge dependency and complete MA edge dependency: The LI missing edge estimation is completely dependent on the MA profile which is determined in pervious stage. In fact, the MA profile is used to create a guidance zone starting from the profile and extending it upwards 50 pixels. This is used so as to find solely the edge objects from the image output of the edge flow algorithm that can be found above (lower row value) the MA profile and that have at least some common support with it Once this step is done, the following steps are necessary for each of these i edge objects:

1. Find the common support between the MA profile and the i-th edge object and cut the MA profile to the common support ($MAcut_i$).
2. Create a mask starting from $MAcut_i$ and extending it upwards 10 pixels and calculate the mean ($IM_{mean_{GT}}$) and standard deviation ($IM_{std_{GT}}$) of the pixel values found in the mask.
3. Create a second mask starting from $MAcut_i$ and extending it up to the i-th edge object. For each pixel found in this mask, determine if it can be defined as an acceptable pixel based on the following equation:

$$|PixelValue - IM_{mean_{GT}}| < IM_{std_{GT}} \Rightarrow AcceptablePixel \quad (22)$$

and determine an $IM_{ratio}$ as the ratio between the number of acceptable pixels found and the total number of pixels considered.

4. Calculate the row distance between the left unconnected end point of the i-th edge object and the first point of $MAcut_i$ ($LT_{y_i}-LT_{y_{MA}}$) and the row distance between the right unconnected end point of the i-th edge object and the last point of $MAcut_i$ ($RT_{y_i}-RT_{y_{MA}}$).
5. Determine that the edge object can be classified as being part of the LI segment if the following two conditions are met:

$$IM_{ratio} > 0.4 \quad (23)$$

$$mean(LT_{y_i}-LT_{y_{MA}}, RT_{y_i}-RT_{y_{MA}}) > 5 \quad (24)$$

The first condition is important in that it avoids classifying an edge object which is found in the lumen since the pixel values in the lumen are considerably lower than $IM_{mean_{GT}}$ and those pixels would therefore not be classified as an acceptable pixel, lowering by a good deal the calculated $IM_{ratio}$. The second condition is necessary so as to not include over-segmented edge objects, which are located too close to the MA profile (i.e., in between the MA and LI profiles.)

6. Repeat steps 1-5 until all edge objects are examined.

Once all of the edge objects are examined, those found to be part of the LI segment (good edge objects) must be tested to see if the distance between two adjacent edges objects is too vast. This is to avoid connecting two edge objects which are too far from each other, which could have a negative effect on the outcome of the final LI profile.

To do this, the good edge objects are considered by adjacent pairs. The Euclidean distance between the two closest unconnected end points of the pair is calculated and if this distance exceeds a certain limit, the good edge objects are classified as belonging to two different LI segments. If the distance calculated is less than the defined limit, then the pair is classified as belonging to the same LI segment. Once all good edge objects have been examined, the final LI segment is determined by those that are part of the longest LI segment found.

The edge objects that are part of the final LI segment are then connected together and regulated using a B-spline to produce the final. LI profile.

Figure 21:
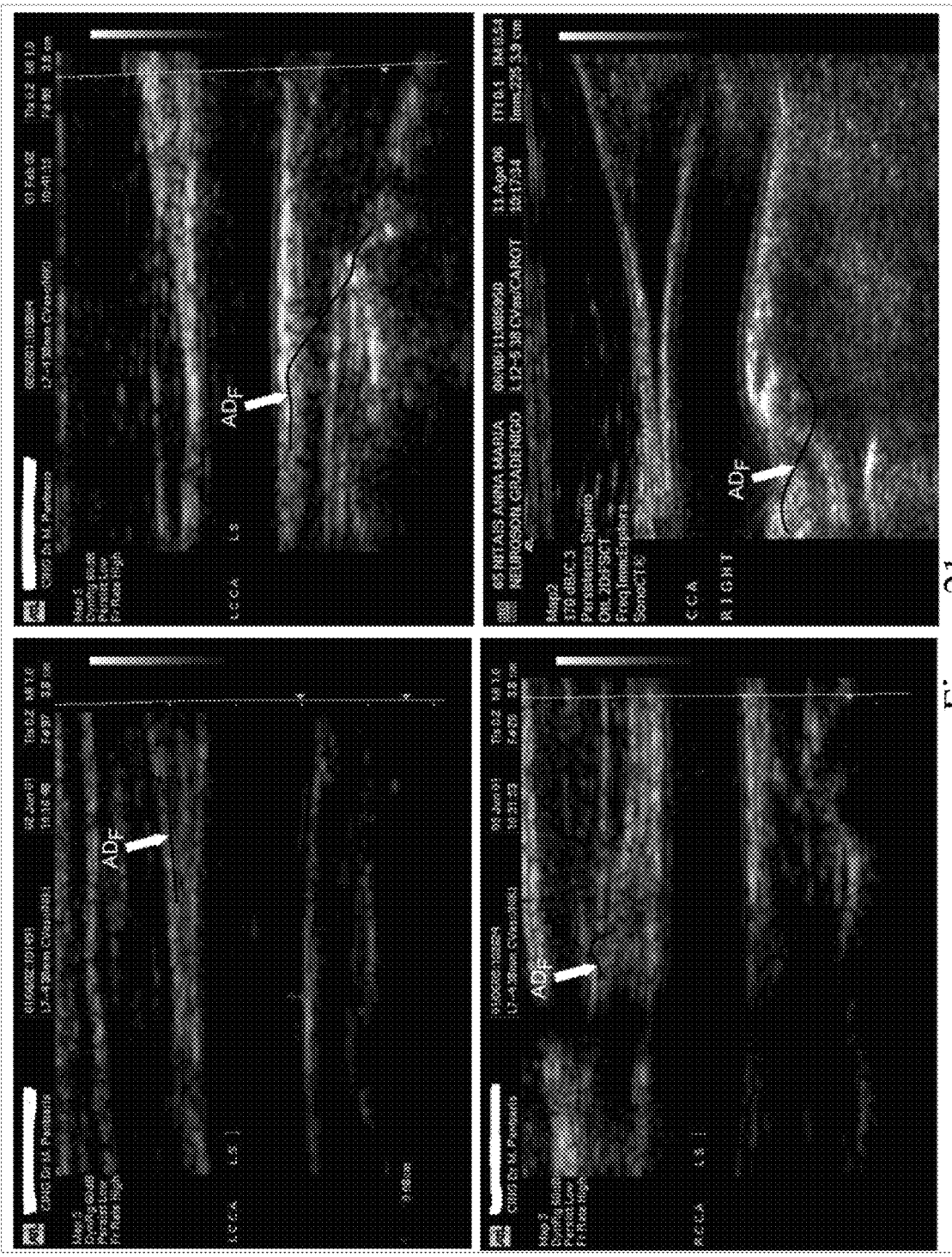
FIG. 21 shows the ADF without Lumen integration.
Figure 22:
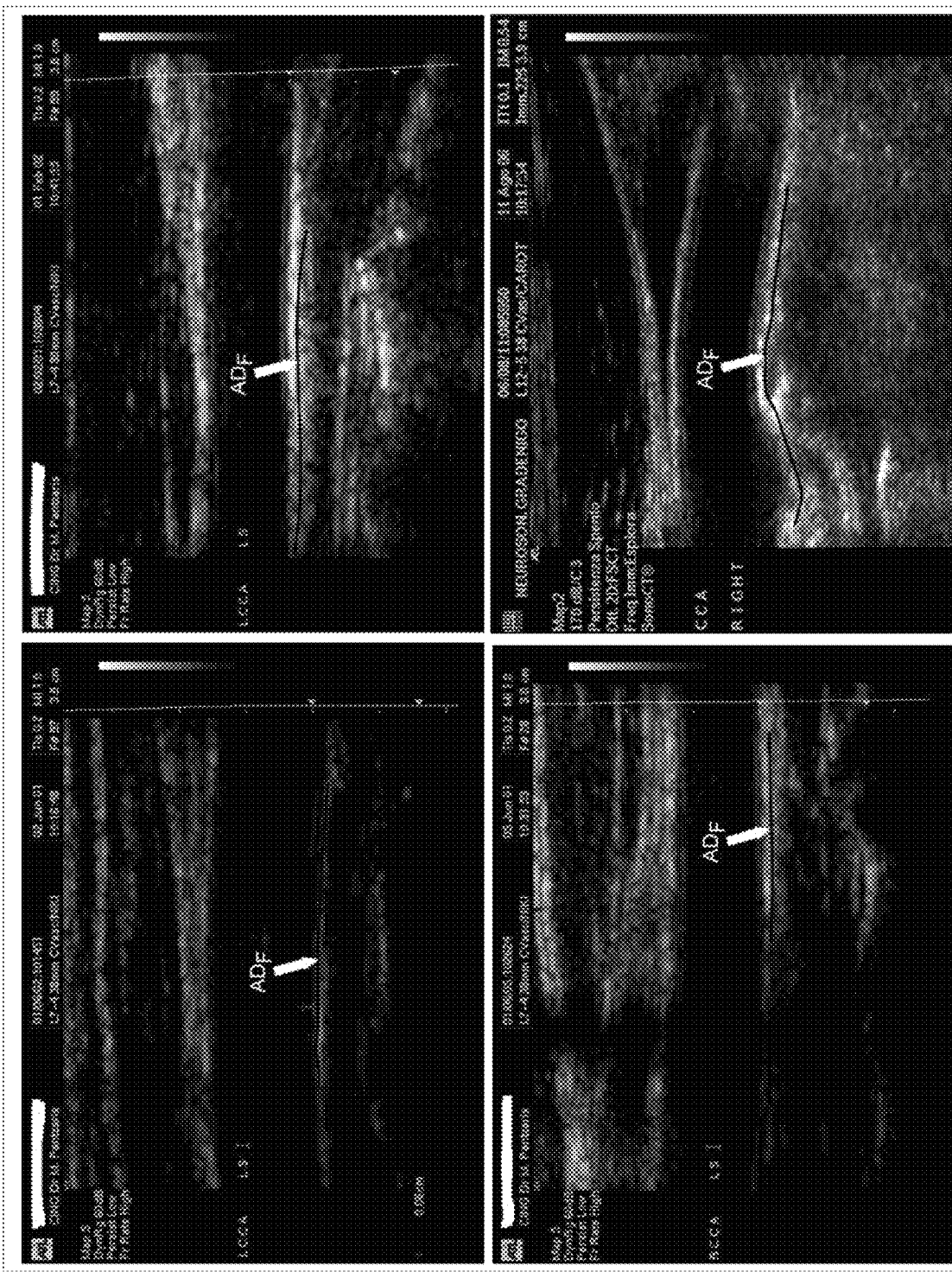
FIG. 22 shows the results of ADF with Lumen integration.
Figure 23:
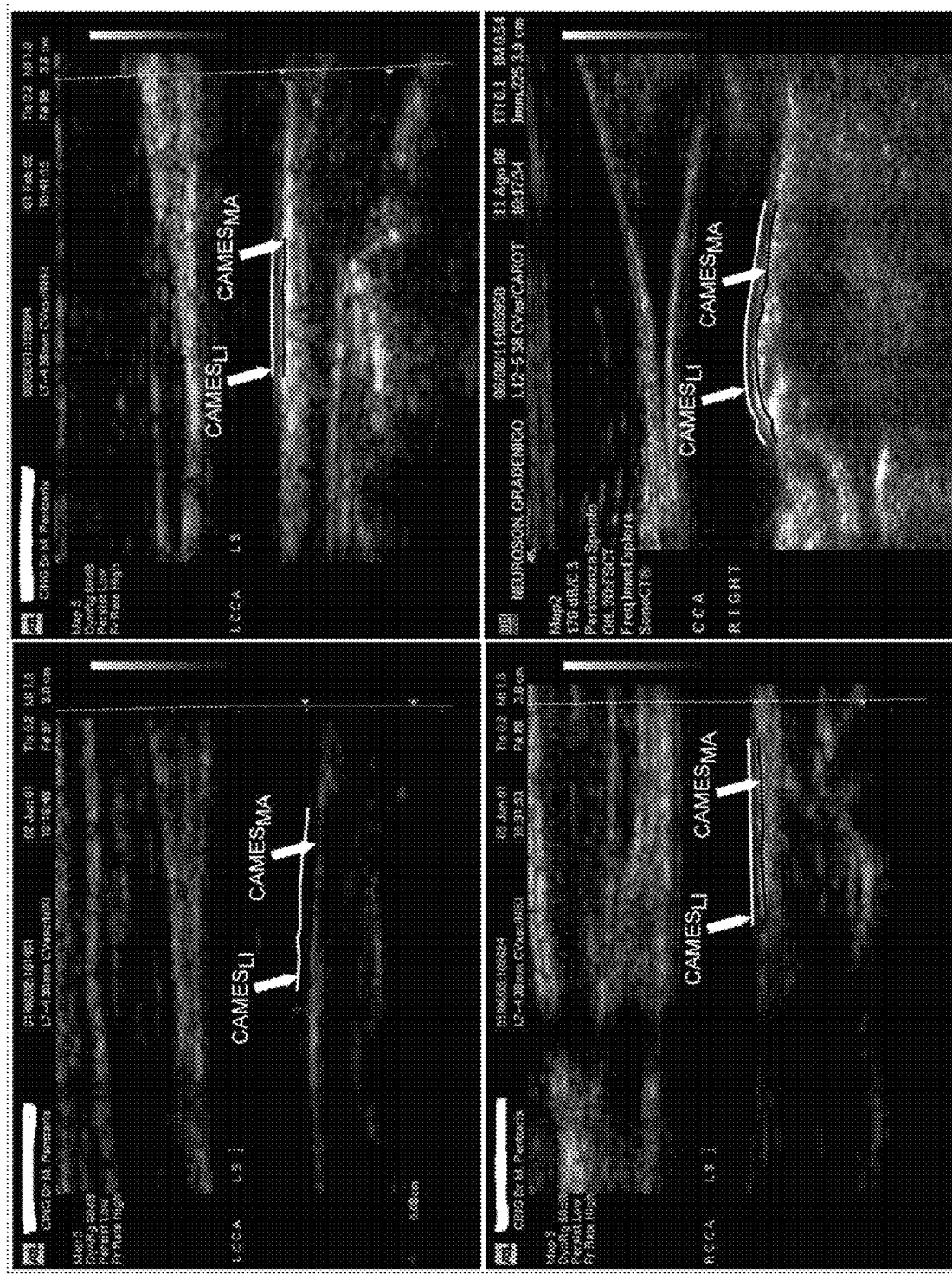
FIG. 23 shows the results of the LIMA borders with Lumen integration.

FIGS. 21, 22 and 23 are the results of the stage I output and stage II output.

FIG. 21 shows the ADF output when the lumen was not integrated. If the lumen check was not integrated, the ADF could be estimated near the Jugular Vein. If the lumen validation system was integrated, the ADF was at the right place as shown in FIG. 22. The results of the segmentation step after stage II on LI/MA segmentation is shown in FIG. 23.

Performance Metric:

The segmentation errors were computed by comparing automated tracings by CALEX and AtheroEdge™ with manual segmentations. We used the Polyline Distance measure (PDM) as performance metric. Given two boundaries B1 and B2, first the distance of the vertices of a boundary B1 from the segments of the boundary B2 is computed. Then, it is computed the dual distance (i.e. the distance of the vertices of B2 from the segments of B1). The final PDM measure is the average distance of the two distances normalized to the overall number of points (i.e. the sum of the points of B1 and B2). It was proved that PDM is almost independent on the number of points of the boundaries. Hence, PDM was proposed as a good metric when in presence of boundaries with a different number of points: in our dataset, the manual profiles had an average number of points of 20, whereas the computer generated boundaries had an average number of points equal to about 250.

Considering the i-th image of the dataset, the segmentation errors for the LI and MA boundaries were defined as:

$$\left.\begin{array}{l} \varepsilon_{LI}^{i} = PDM(AtheroEdge^{TM}_{LI}, GT_{LI}) \\ \varepsilon_{MA}^{i} = PDM(AtheroEdge^{TM}_{MA}, GT_{MA}) \end{array}\right\} \quad (3)$$

where $AtheroEdge^{TM}_{LI}$ (CAMES) and $AtheroEdge^{TM}_{MA}$ (CAMES) are the LI and MA profiles traced by AtheroEdge™, and $GT_{LI}$ and $GT_{MA}$ are the ground-truth boundaries. Analogous errors were defined for CALEX boundaries. The mean LI and MA performance was computed as:

$$\left.\begin{array}{l} \overline{\varepsilon}_{LI} = \frac{1}{N}\sum_{i}\varepsilon_{LI}^{i} \\ \overline{\varepsilon}_{MA} = \frac{1}{N}\sum_{i}\varepsilon_{MA}^{i} \end{array}\right\} \quad (4)$$

where N is the total number of images of the testing database.

The IMT value was computed as distance between the LI and the MA profiles on every single image. Therefore, for every image, we computed an IMT value for CALEX (called CALEX IMT), for AtheroEdge™ (or CAMES IMT) and for ground-truth (GT IMT). The IMT measurement bias was defined as:

$$\left.\begin{array}{l} \mu_{AtheroEdge^{TM}}^{i} = |AtheroEdge^{TM}_{IMT}^{i} - GT_{IMT}^{i}| \\ \mu_{CALEX}^{i} = |CALEX_{IMT}^{i} - GT_{IMT}^{i}| \end{array}\right\} \quad (5)$$

The overall system performance of the system in terms of IMT measurement was computed as:

$$\left.\begin{array}{l} \overline{\mu}_{AtheroEdge^{TM}} = \frac{1}{N}\sum_{i}\mu_{AtheroEdge^{TM}}^{i} \\ \overline{\mu}_{CALEX} = \frac{1}{N}\sum_{i}\mu_{CALEX}^{i} \end{array}\right\} \quad (6)$$

For performance evaluation we compare AtheroEdge™ with CALEX system published by on automated IMT measurement system (Molinari F, Zeng G, Suri J S. An integrated approach to computer-based automated tracing and its validation for 200 common carotid arterial wall ultrasound images: A new technique. J Ultras Med. 2010; 29:399-418).

Table 1 reports the overall LI (first row) and MA (second row) segmentation errors for the AtheroEdge™ (first column) and CALEX (second column) techniques when Lumen validation system was not integrated into the system.

Table 2 reports the overall LI (first row) and MA (second row) segmentation errors for the AtheroEdge™ (first column) and CALEX (second column) techniques when Lumen validation system was integrated into the system. AtheroEdge™ outperformed CALEX in both LI and MA tracings, leading to an improvement of the distal wall segmentation error equal to 8% for LI and 42% for MA. The average LI and MA segmentation errors using AtheroEdge™ were 0.081±0.099 mm and 0.082±0.197 mm, respectively. The Percent. Statistic Test indicated that AtheroEdge™ profiles could be considered as equivalent to manually traced ones. Considering n=3 and N=365; we obtained p=0.5 and θ=0.051. Therefore, considering α=0.05, the Percent Statistic Test is passed when Z0>0.448. AtheroEdge™ showed Z0 scores equal to 0.545 (for the LI interface) and of 0.530 (for the MA interface), while CALEX showed Z0 scores of 0.478 (LI) and 0.451 (MA).

IMT Measurement Bias

The third row of Table 2 reports the IMT measurement bias. AtheroEdge™ showed a measurement error significantly lower than CALEX (Student's t-test, p<10-3): AtheroEdge™ error was as low as 0.078±0.112 mm, whereas CALEX showed a higher error equal to 0.121±0.334 mm. AtheroEdge™ showed an improvement over CALEX by 36%.

Table 3 reports the IMT value measured by AtheroEdge™ (first column), CALEX (second column) and ground-truth (GT) (third column). It can be noticed that AtheroEdge™ demonstrated a very accurate IMT computation equal to 0.91±0.45 mm, which is very close to ground-truth of 0.95±0.41 mm. On the contrary, CALEX measurement was less accurate resulting in the IMT value of 0.83±0.39 mm.

Another way of interpretation is by computing the figure-of-merit (FoM) in % as:

$$FoM_{AtheroEdge^{TM}} = 100 - \frac{\overline{GT}_{IMT} - \overline{AtheroEdge^{TM}}_{IMT}}{\overline{GT}_{IMT}} \cdot 100 \quad (12)$$

$$FoM_{CALEX} = 100 - \frac{\overline{GT}_{IMT} - \frac{\overline{GT}_{IMT}}{CALEX_{IMT}}}{\overline{GT}_{IMT}} \cdot 100$$

Using the above definitions, the FoM for CALEX came out to be 87.4%, while AtheroEdge™ was much superior yielding to 95.8%. This clearly demonstrates the how close and reproducible the IMTs are with AtheroEdge™ compared to CALEX.

Figure 24:
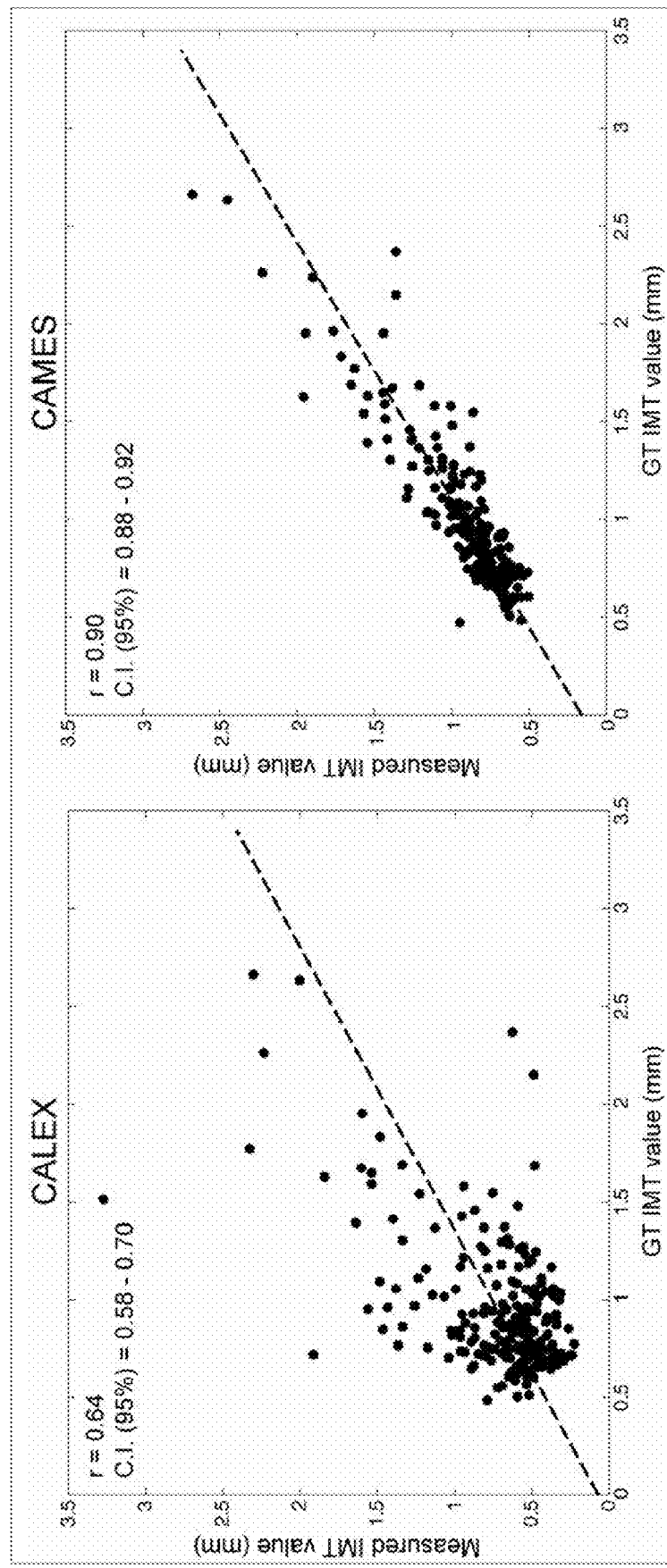
FIG. 24 reports the scatter diagrams for the present embodiments (denoted herein as the AtheroEdge™ system) vs. CALEX system (citation of CALEX: Molinari F, Zeng G, Suri J S. An integrated approach to computer-based automated tracing and its validation for 200 common carotid arterial wall ultrasound images: A new technique. J Ultras Med. 2010; 29:399-418).

Scatter Diagrams:

FIG. 24 reports the scatter diagrams showing the CALEX (on the left) and AtheroEdge™ (on the right) IMT estimates with respect to GT. AtheroEdge™ showed a correlation coefficient as high as 0.90 (95% C.I.=0.88-0.92), whereas the correlation coefficient of CALEX was only of 0.64 (95% C.I.=0.58-0.70).

Figure 25:
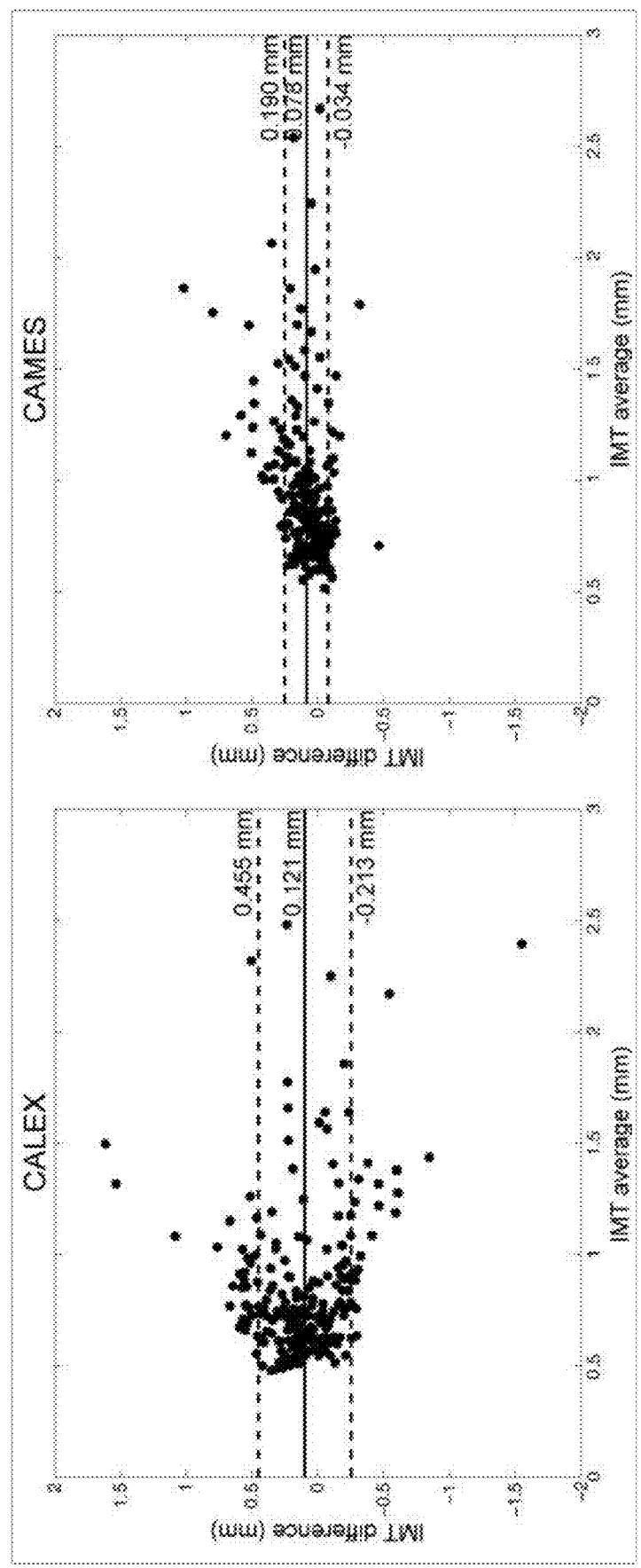
FIG. 25 reports the Bland-Altman Plots for AtheroEdge™ system vs. CALEX system.

FIG. 25 shows the Bland-Altmann plots for CALEX (left) and AtheroEdge™ (right). Clearly, AtheroEdge™ estimates are more accurate than CALEX.

FIG. 26 is a processing flow diagram illustrating an example embodiment of a computer-implemented system and method for intima-media thickness (IMT) measurements using a validation embedded segmentation method as described herein. The method 2600 of an example embodiment includes: receiving biomedical imaging data and patient demographic data corresponding to a current scan of a patient (processing block 2610); checking the biomedical imaging data in real-time to determine if an artery of the patient has a calcium deposit in a proximal wall of the artery (processing block 2612); acquiring arterial data of the patient as a combination of longitudinal B-mode and transverse B-mode data (processing block 2614); using a data processor to automatically recognize the artery by embedding anatomic information (processing block 2616); using the data processor to calibrate a region of interest around the automatically recognized artery (processing block 2618); and determining the intima-media thickness (IMT) of an arterial wall of the automatically recognized artery (processing block 2620).

Figure 27:
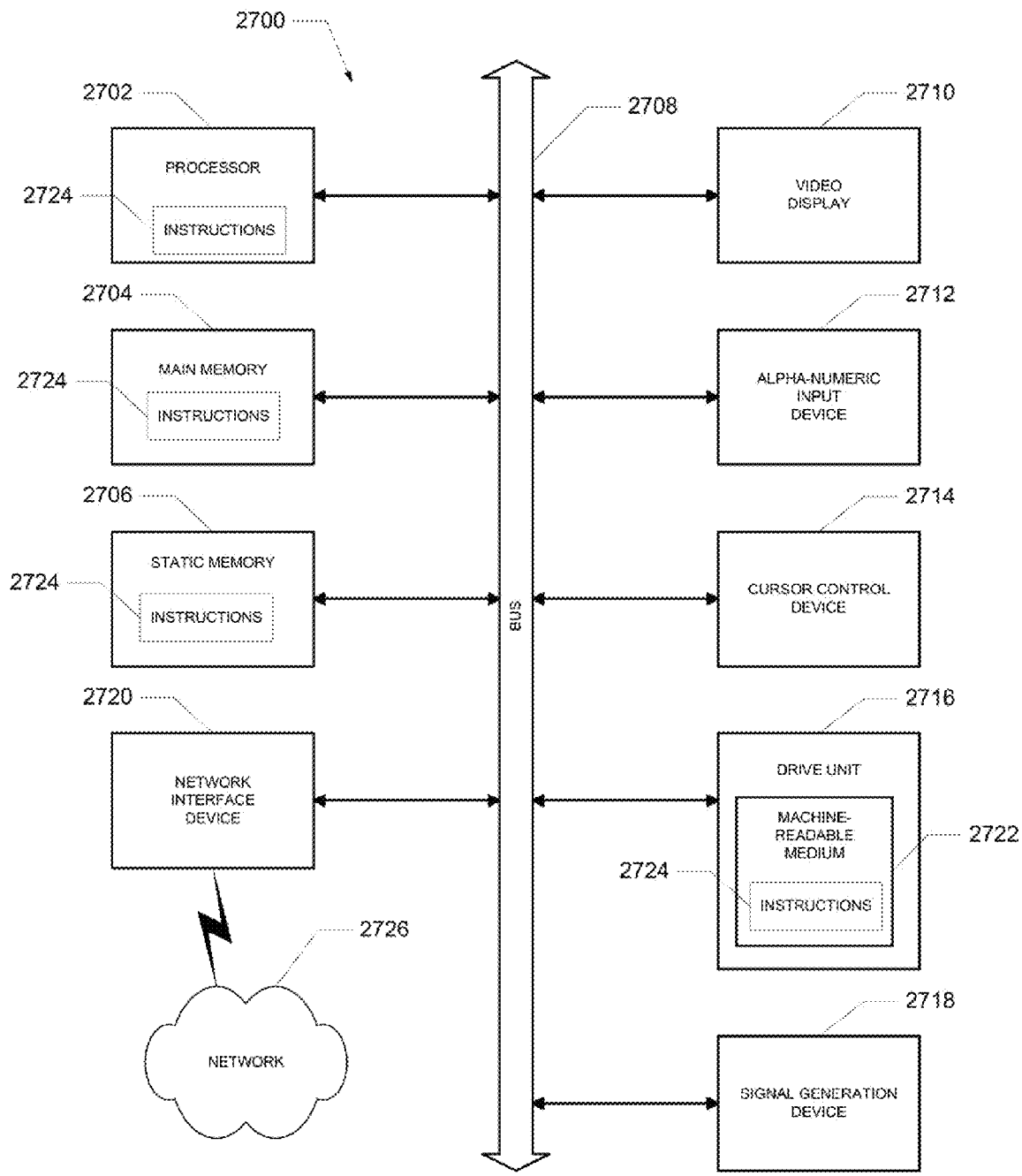
FIG. 27 shows a diagrammatic representation of machine in the example form of a computer system within which a set of instructions when executed may cause the machine to perform any one or more of the methodologies discussed herein.

FIG. 27 shows a diagrammatic representation of machine in the example form of a computer system 2700 within which a set of instructions when executed may cause the machine to perform any one or more of the methodologies discussed herein. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" can also be taken to include any collection of machines that individually or jointly execute a set (or multiple sets) of instructions to perform any one or more of the methodologies discussed herein.

The example computer system 2700 includes a processor 2702 (e.g., a central processing unit (CPU), a graphics processing unit (GPU), or both), a main memory 2704 and a static memory 2706, which communicate with each other via a bus 2708. The computer system 2700 may further include a video display unit 2710 (e.g., a liquid crystal display (LCD) or a cathode ray tube (CRT)). The computer system 2700 also includes an input device 2712 (e.g., a keyboard), a cursor control device 2714 (e.g., a mouse), a disk drive unit 2716, a signal generation device 2718 (e.g., a speaker) and a network interface device 2720.

The disk drive unit 2716 includes a machine-readable medium 2722 on which is stored one or more sets of instructions (e.g., software 2724) embodying any one or more of the methodologies or functions described herein. The instructions 2724 may also reside, completely or at least partially, within the main memory 2704, the static memory 2706, and/or within the processor 2702 during execution thereof by the computer system 2700. The main memory 2704 and the processor 2702 also may constitute machine-readable media. The instructions 2724 may further be transmitted or received over a network 2726 via the network interface device 2720. While the machine-readable medium 2722 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" can also be taken to include any non-transitory medium that is capable of storing, encoding or carrying a set of instructions for execution by the machine and that cause the machine to perform any one or more of the methodologies of the various embodiments, or that is capable of storing, encoding or carrying data structures utilized by or associated with such a set of instructions. The term "machine-readable medium" can accordingly be taken to include, but not be limited to, solid-state memories, optical media, and magnetic media.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

TABLE 1

(IMT values without Lumen)

| | AtheroEdge ™ |
|---|---|
| LI Error | 1.03 ± 0.85 px |
| | 0.063 ± 0.052 mm |
| MA Error | 1.15 ± 0.83 px |
| | 0.070 ± 0.050 mm |

TABLE 1-continued (IMT values without Lumen)

| | AtheroEdge ™ |
|---|---|
| IMT Error | 1.53 ± 1.89 px |
| | 0.093 ± 0.116 mm |
| IMT value | 13.36 ± 7.07 px |
| | 0.82 ± 0.44 mm |

TABLE 2

Performance and Benchmarking
Overall system performance for AtheroEdge ™ with
Lumen Integration (first column) Vs. CALEX (second column).

| | AtheroEdge ™ | CALEX | Error reduction |
|---|---|---|---|
| LI Error ($\bar{\epsilon}_{LI}$) | 0.081 ± 0.099 mm | 0.088 ± 0.132 mm | 8% |
| MA Error ($\bar{\epsilon}_{MA}$) | 0.082 ± 0.197 mm | 0.141 ± 0.201 mm | 42% |
| IMT Bias ($\bar{\mu}$) | 0.078 ± 0.112 mm | 0.121 ± 0.334 mm | 36% |

TABLE 3

Average IMT and Figure of Merit (FoM)
Average IMT value by AtheroEdge ™ (first column) and
CALEX (second column), as compared to ground-truth
(third column). The second row reports the figure-of-merit (FoM).

| | AtheroEdge ™ | CALEX | Ground-Truth |
|---|---|---|---|
| IMT measurement | 0.91 ± 0.44 mm | 0.83 ± 0.39 mm | 0.95 ± 0.39 mm |
| FoM | 95.8% | 87.4% | — |

TABLE 4

AtheroEdge ™ parameters
AtheroEdge ™ parameters and experimental values used.

| Parameter | Value | Experimental Range and Effect |
|---|---|---|
| Stage-I ($AD_F$ Identification) | | |
| Scale Parameter ($\sigma$) | 8 pixels | $\sigma$ = 6-10 pixels. Scale of the 1$^{st}$ order Gaussian Kernel derivative during the stage I process. |
| ROI width for lumen validation ($ROI_{Lumen}$) | 30 pixels | Sequence of points above $AD_F$ to check for lumen test. |
| Lumen test failure threshold ($T_{Lumen}$) | 15 pixels | Threshold for passing the lumen test. |
| Spike detection threshold ($T_{Spike}$) | 15 pixels | $T_{Spike}$ = 12-16 pixels. Determines the difference between consecutive points of a profile that we consider a spike. |
| Stage II (LI/MA segmentation) | | |
| MRFOAM Calibration Factor ($\eta_{MRFOAM}$) | 0.3 mm | Determines noise robustness and LI/MA accuracy. |
| Gaussian Kernel size ($\theta_1$) | 5 pixels | $\theta_1 = \eta_{MRFOAM}/\tau_{Nicosia}$ Implements the GoG filter. ($\tau_{Nicosia}$ is the conversion factor of Table 1) |
| Gaussian Kernel size ($\theta_2$) | 10 pixels | $\theta_2 = 2\theta_1$ Implements the GoG filter |
| Gaussian Kernel size ($\theta_3$) | 5 pixels | $\theta_3 = \eta_{MRFOAM}/\tau_{Nicosia}$ Regularization parameter. ($\tau_{Nicosia}$ is the conversion factor of Table 1) |
| Gaussian scale $\sigma_1$ and $\sigma_3$ | 2 pixels | $\sigma_1 = [\theta_1/3]$ |
| Gaussian scale $\sigma_2$ | 3 pixels | |

What is claimed is:

1. A computer-implemented method comprising:
receiving biomedical imaging data and patient demographic data corresponding to a current scan of a patient;
real time checking if the artery has calcium deposit in the proximal wall;
acquiring the arterial data as a combination of longitudinal B-mode and transverse B-mode;
using a data processor to automatically recognize the far adventitia border of the artery using multi-resolution approach;
using the data processor to automatically recognize the anatomic landmark lumen artery by using a classifier;
using the data processor to automatically validate the far adventitia border with respect the anatomic landmark lumen artery;
using the processor to automatically correct the far adventitia border;
using the data processor to calibrate the region of interest around the automatically validated and corrected recognized artery to determine the segmented lumen-intima and media-adventitia borders;
using the data processor to calibrate a region of interest using an edge flow method to compute the lumen-intima and media-adventitia borders, and
determining the intima-media thickness of the arterial wall.

2. The method as claimed in claim 1 wherein the biomedical imaging data comprises a combination of two-dimensional (2D) longitudinal B-mode and two-dimensional (2D) transverse B-mode ultrasound images.

3. The method as claimed in claim 1 wherein the edges of the far adventitia border are determined in coarse resolution.

4. The method as claimed in claim 1 wherein the edges of the far adventitia border are determined in coarse resolution and up-sampled back onto the original high resolution image.

5. The method as claimed in claim 1 wherein the artery location can be validated using the lumen as an anatomic information and modeled as a mixture model.

6. The method as claimed in claim 1 wherein the validated and corrected using anatomic landmark lumen artery is automatically segmented using a classifier.

7. The method as claimed in claim 1 wherein the method where prior to calibration stage for lumen-intima and media-adventitia borders, a noise is reduced in real time in the region of interest where the automated artery is recognized.

8. The method as claimed in claim 1 wherein the method is used for monitoring the IMT for patients which are under clinical trials.

9. The method as claimed in claim 1 wherein the method is used computing the IMT of a batch of patients in the database automatically using the knowledge of ethnicity, demographics, age and gender.

10. The method as claimed in claim 1 wherein the method is controlled by the user or vascular surgeon or trained sonographers or vascular radiologist, neuroradiologist or a cardiologist.

11. A computer-implemented method comprising:
receiving biomedical imaging data and patient demographic data corresponding to a current scan of a patient;
real time checking if the artery has calcium deposit in the proximal wall;
acquiring the arterial data as a combination of longitudinal B-mode and transverse B-mode;
using a data processor to automatically recognize the far adventitia border of the artery using multi-resolution approach;
using the data processor to automatically recognize the far adventitia borders by convolution in coarse resolution using a higher order derivative of Gaussian kernels, a scale using a priori anatomic information and using a database of ultrasound images;
using the data processor to automatically recognize the anatomic landmark lumen artery by using a classifier;
using the data processor to automatically validate the far adventitia border with respect the anatomic landmark lumen artery;
using the data processor to automatically correct the far adventitia border;
using the data processor to calibrate the region of interest around the automatically validated and corrected recognized artery to determine the segmented lumen-intima and media-adventitia borders; and
determining the intima-media thickness of the arterial wall.

12. The method as claimed in claim 11 wherein the method where the automated recognition using higher order derivative is with and without calcium present in the arterial proximal wall.

13. The method as claimed in claim 11 wherein the method where calibration is guided by an edge flow method.

14. The method as claimed in claim 11 wherein the method where calibration which is a derivative of Gaussian image convolved with a scale parameter Gaussian Kernel in the region of interest.

15. The method as claimed in claim 11 wherein a derivative of Gaussian filter is applied to a speckle free region of interest on the original image guided by the automated recognition artery.

* * * * *